(12) United States Patent
Zhang et al.

(10) Patent No.: US 7,211,655 B2
(45) Date of Patent: *May 1, 2007

(54) METHODS FOR IDENTIFYING MODULATORS OF TRANSCRIPTIONAL ACTIVATOR PROTEIN INTERACTIONS

(75) Inventors: Xiaokui Zhang, New York, NY (US); Curt Horvath, New York, NY (US); Melissa H. Wrzeszczynska, New York, NY (US); James E. Darnell, Jr., Larchmont, NY (US)

(73) Assignee: The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/218,272

(22) Filed: Sep. 1, 2005

(65) Prior Publication Data

US 2006/0020112 A1    Jan. 26, 2006

Related U.S. Application Data

(60) Division of application No. 10/090,185, filed on Mar. 4, 2002, now Pat. No. 6,960,647, which is a continuation of application No. 09/387,418, filed on Aug. 31, 1999, now Pat. No. 6,391,572.

(51) Int. Cl.
*C07H 21/02* (2006.01)
*C07K 14/00* (2006.01)
*C12N 15/63* (2006.01)

(52) U.S. Cl. ..................... 536/23.1; 530/350

(58) Field of Classification Search .............. None
See application file for complete search history.

(56) References Cited

U.S. PATENT DOCUMENTS 5,716,622 A    2/1998    Darnell, Jr. et al.

FOREIGN PATENT DOCUMENTS

| WO | WO 93/19179 | 12/1993 |
|----|-------------|---------|
| WO | WO 95/08629 | 3/1995  |
| WO | WO 96/20954 | 7/1996  |
| WO | WO 99/14322 | 3/1999  |

OTHER PUBLICATIONS

Bromberg et al., 1998, Mol Cell Biol, 18:2553-8.
Carey, 1998, Cell, 92:5-8.
Darrnell, 1997, Science, 277:1630-5.
Horvath et al., 1996, Mol Cell Biol, 16:6957-64.
Roeder, 1997, Trends Biochem Sci, 21:327-35.
Schaefer et al., 1997, Mol Cell Biol, 17:5307-16.
Schaefer et al., 1995, Proc Natl Acad Sci USA, 92:9097-101.

*Primary Examiner*—Nancy Vogel
*Assistant Examiner*—Michele K. Joike
(74) *Attorney, Agent, or Firm*—Klauber & Jackson

(57) ABSTRACT

The present invention relates to methods for identifying interacting regions of transcription factors, and methods for identifying agents which modulate the interactions, useful for affecting gene regulation, for example, cellular transformation. A site within residues 130–154 and within residues 343–358 in Stat3 were found to interact with the transcription factor c-Jun. On c-Jun, a site within residues 105 and 334, and more particularly, between 105 and 263, interact with Stat3. These sites of interactions permit methods for identifying agents which modulate the interaction between these transcription factors to modulate gene transcription.

3 Claims, 9 Drawing Sheets

α-c-Jun Blot

FIG. 4A

```
             137  141 144  148  151                      346 348 350
Stat3   AAVVTEKQQMLEQHLQDVRKR  ············  GVQFTIKMRLLVK
Stat1   STVMLDKQKELDSKVRNVKDK  ············  GVQFTMKLRLLVK
Stat2   ETEVESQQHEIESRILDLRAM  ············  GSKFTMRIRLLVR
Stat4   SSSVSERQRNVEHKVAAIKNS  ············  LIQFTMKLRLLIK
Stat5a  HLQINQTFEELRLVTQDTENE  ············  QTKFAATMRLLVG
Stat6   -FHNKQEELKFKTGLRRLQHR  ············  QTKFQAGMRFLLG
              Region 1                              Region 2
```

FIG. 4B

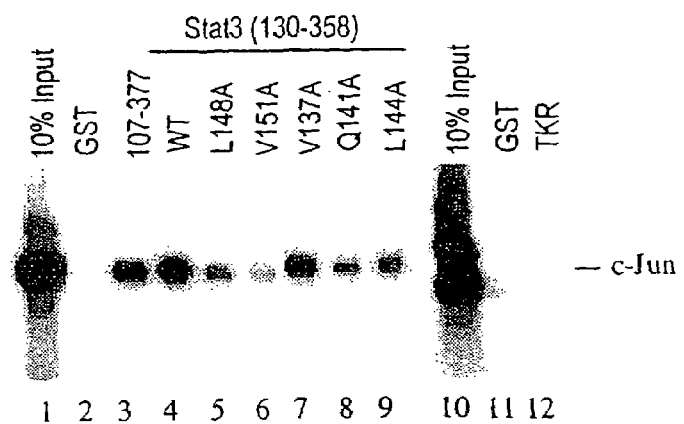

METHODS FOR IDENTIFYING MODULATORS OF TRANSCRIPTIONAL ACTIVATOR PROTEIN INTERACTIONS

CROSS REFERENCE TO RELATED APPLICATIONS

This application is a Divisional Application of application U.S. Ser. No. 10/090,185, filed Mar. 4, 2002, now U.S. Pat. No. 6,960,647, which is a continuation of application having U.S. Ser. No. 09/387,418, filed Aug. 31, 1999, now U.S. Pat. No. 6,391,572. Applicants claim the benefit of these applications under 35 U.S.C. §120, the contents all of which are incorporated herein by reference in their entireties.

GOVERNMENTAL SUPPORT

The research leading to the present invention was supported in part, by a grant from NIH grants AI32489, AI34420 and CA09673. Accordingly, the Government may have certain rights in the invention.

FIELD OF THE INVENTION

The present invention relates to identifying interacting regions of transcription factors, and methods for identifying agents which modulate the interactions, useful for affecting gene regulation, for example, in cellular transformation.

BACKGROUND OF THE INVENTION

Clustered specific DNA binding sites for an array of activating transcription factors, plus proteins that bend DNA to facilitate contact between bound proteins, have been documented for a number of vertebrate genes (15, 21, 25, 37). These composite structures have been called enhanceosomes (8). The TCR-(15) and the IFN-(25) enhanceosomes, which are assembled in response to dimerization of the T cell receptor or double-stranded RNA, have been most thoroughly explored. Two classes of genes that are very likely dependent upon enhanceosome assembly have received great attention: genes expressed in a tissue-specific manner that acquire multiple binding proteins during development, and genes that are acutely activated by an external stimulus. These latter structures hold appeal for study because they can be examined in cultured cells where induced synchronous changes occur in all the cells under observation, allowing the acute assembly and disassembly of proteins in an enhanceosome to be potentially revealed.

The Stat family of transcription factors (Darnell, 1997; Stark et al., 1998; U.S. application Ser. No. 08/212,185, filed Mar. 11, 1994 and U.S. Pat. No. 5,716,622; all of the foregoing incorporated herein by reference in their entireties) is activated by polypeptide ligands attaching to specific cell surface receptors, and after tyrosine phosphorylation, dimerization and translocation to the nucleus, can participate within minutes in gene activation (11). It seems likely that Stat molecules bind DNA regions where pre-enhanceosome structures exist (26, 27) and that the arrival of activated Stat dimer(s) is key to forming an active enhanceosome (27). Such a possibility is suggested by experiments showing closely spaced binding sites for Stats and other proteins in the response elements for a number of genes (17, 24, 27, 41). Furthermore DNase and permanganate treatment of cell nuclei revealed proteins bound at or near Stat1 sites before polypeptide treatment. This was followed by detection of Stat molecules binding close to the same DNA regions after induction (26).

One intensively studied set of physiologically important genes that are transcriptionally induced in the liver are the "acute phase response proteins" which increase in the wake of bacterial infections and other toxic assaults. IL-6 stimulation of hepatocytes, via the activation of Stat3, is thought to be the main trigger for inducing the acute phase genes (18). One of the best studied enhancers for acute phase response genes is that of the $\alpha_2$-macroglobulin enhancer [(20), reviewed in (18)], a DNA fragment 100 bases long with binding sites for both Stat3 (also called GAS site) and for AP-1, which includes members of the Fos, Jun and ATF families of transcription factors. Extracts from liver nuclei of IL-6 treated animals or transformed hepatocytes (hepatoma cells) in culture indicated induced binding to this region. Since Stat3 and c-Jun interacted in yeast 2-hybrid assays and cooperated in maximizing the transcription responses of reporter genes containing the ~100 bp enhancer (30, 31), it seemed likely that this genomic region might form a Stat-dependent enhanceosome.

It is towards identifying particular regions of transcription factor interactions responsible for transcriptional activation, and the use of this information in the design of methods and the subsequent identification of agents capable of modulation the interaction, that the present invention is directed.

SUMMARY OF THE INVENTION

In its broadest aspect, the present invention is directed to methods for identifying an agent capable of modulating the interaction between a transcription factor and a Stat protein comprising the steps of (a) providing said transcription factor or a fragment thereof;
(b) providing a Stat protein fragment comprising a region within from about residue 107 to about residue 377 of the Stat protein;
(c) incubating mixtures of the transcription factor or fragment thereof and the Stat protein fragment with and without said agent;
(d) detecting the extent of interaction between the transcription factor or fragment thereof and the Stat protein fragment in each of the mixtures; and
(e) identifying an agent as capable of modulating said interaction as one which alters the extent of interaction between the transcription factor or fragment thereof and the Stat protein fragment.

The agent may be capable of modulating cellular transformation. The Stat protein fragment of the foregoing method may comprise the coiled-coil domain of the Stat protein and the first three-strands of the DNA-binding domain of the Stat protein. Non-limiting examples of Stat protein include Stat1, Stat2, Stat3, Stat4, Stat5 or Stat6. For example, for Stat3, fragments may include about residue 107 to about residue 358, about residue 130 to about residue 358, about residue 155 to about residue 377, about residue 193 to about residue 377, about residue 249 to about residue 377, or about residue 282 to about residue 377. Particular suitable fragments include those set forth as SEQ ID NO:9, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24 and SEQ ID NO:25. The Stat protein or fragment may be labeled with a detectable label, for example, a GST fusion sequence or an epitope tag.

The transcription factor used in the above-described method may be a member of the JUN, the FOS, or the ATF families of transcription factors. For example, a JUN transcription factor may be c-Jun, JunB and JunD. A FOS transcription factor may be c-Fos, FosB, Fra-1 and Fra-2. An ATF transcription factor may be ATF-1, ATF-2, ATF-3 and ATF-4. These examples are merely illustrative and non-limiting. The transcription factor fragment may include the COOH-terminal region, or the bZIP region.

In one example, the transcription factor is c-Jun. A fragment of c-Jun may include the region of about residue 105 to about residue 334 of c-Jun, or the region of about residue 105 to about residue 263 of c-Jun. The transcription factor or fragment thereof may be labeled with a detectable label, for example, a radiolabel.

The detection of the extent of interaction of the foregoing method may be carried out for example using the techniques of is performed by GST protein association assay, coimmunoprecipitation, eletrophoretic mobility shift assay (EMSA), or the yeast 2-hybrid system.

In one example wherein the Stat protein is Stat3, the agent modulates the interaction between the transcription factor and Stat3 protein at residues of said Stat3 protein such as but not limited to residues 130–154, residues 343–358, and the combination thereof. The agent may be a Stat protein antagonist or agonist. In the example wherein the transcription factor is c-Jun, the modulation of interaction may occur at about residue 105 up to about 334 of c-Jun, about residue 105 up to about 334 of c-Jun, or about residues 105–263 of c-Jun.

In another aspect of the present invention, methods are provided for identifying an agent capable of modulating the transcriptional cooperation between a transcription factor and a Stat protein comprising the steps of:
 (a) providing a transiently transfected cell bearing a Stat-inducible reporter gene;
 (b) introducing into the cell a transcriptionally cooperative combination of a wild-type Stat protein or mutant thereof, and a wild-type transcription factor or mutant thereof;
 (c) inducing the expression of the reporter gene;
 (d) determining the extent of expression of the reporter gene in the presence and absence of said agent; and
 (e) identifying an agent capable of modulating said interaction as one able to alter the expression of the reporter gene.

The agent is capable of modulating cellular transformation. The Stat protein or mutant thereof comprises the coiled-coil domain of said Stat protein and the first three β-strands of the DNA-binding domain of said Stat protein. Non-limiting examples of Stat proteins suitable for the practice of the foregoing method include Stat1, Stat2, Stat3, Stat4, Stat5 or Stat6.

In the example wherein the Stat protein is Stat3, the agent may modulate the interaction between the transcription factor and said Stat3 protein at residues of the Stat3 protein of residues 130–154, residues 343–358, or the combination. In another example, the Stat3 mutant has at least one mutation in a region of the native Stat3 sequence at positions selected from the group consisting of residues 130–154, residues 343–358, and the combination thereof. Examples of particular mutants include Stat3(L148A) (SEQ ID NO:30), Stat3(V151A) (SEQ ID NO:31), and Stat3(T346A, K348A, R350A) (SEQ ID NO:29).

The Stat protein or mutant thereof is labeled with a detectable label, for example, a GST fusion sequence or an epitope tag.

Transcription factors useful in the above method include but are not limited to members of the JUN, the FOS, and the ATF families of transcription factors. For example, a JUN transcription factor may be c-Jun, JunB and JunD. A FOS transcription factor may be c-Fos, FosB, Fra-1 and Fra-2. An ATF transcription factor may be ATF-1, ATF-2, ATF-3 and ATF-4. The transcription factor or fragment thereof may be labeled with a detectable label, for example, a radiolabel.

In the example wherein the transcription factor is c-Jun, the agent may modulate the transcriptional cooperation between the c-Jun and Stat3 protein at residues of the c-Jun protein at residues 105–334. The c-Jun interaction regions may be within residues about 105 and up to about 334, or residues about 105 to about 263.

In another broad aspect of the present invention, methods are provided for identifying mutants in a transcription factor or Stat molecule, or in both, wherein the mutant is capable of modulating the transcriptional cooperation between the transcription factor and the Stat protein. The method comprises:
 (a) providing a transiently transfected cell bearing a Stat-inducible reporter gene;
 (b) introducing into the cell a wild-type Stat protein or mutant thereof; and a wild-type transcription factor or mutant thereof, wherein at least one of the introduced Stat protein or transcription factor is mutant;
 (c) inducing the expression of said reporter gene;
 (e) determining the extent of expression of the reporter gene compared to that extent in a cell having a wild-type form of at least one of the mutant transcription factor or the mutant Stat protein; and
 (f) identifying an mutant as one capable of modulating the interaction as one able to alter the expression of the reporter gene.

The Stat protein or mutant thereof may comprise the coiled-coil domain of said Stat protein and the first three β-strands of the DNA-binding domain of said Stat protein. Non-limiting examples of Stat protein include Stat1, Stat2, Stat3, Stat4, Stat5 and Stat6. In the example of Stat3, the mutation may modulate the transcriptional cooperation between the transcription factor and Stat3 at residues of said Stat3 protein such as but not limited to residues 130–154, residues 343–358, and the combination thereof. The Stat3 mutant may have at least one mutation in a region of the native Stat3 sequence at positions within residues 130–154, residues 343–358, or the combination thereof. Particular non-limiting examples include Stat3(L148A) (SEQ ID NO:30), Stat3(V150A) (SEQ ID NO:31), and Stat3(T346A, K348A, R350A) (SEQ ID NO:29).

The Stat protein or mutant thereof may be labeled with a detectable label, such as a GST fusion sequence or an epitope tag.

In the practice of the foregoing method, the transcription factor may be a member of the JUN, the FOS, or the ATF families of transcription factors. For example, a JUN transcription factor may be c-Jun, JunB and JunD. A FOS transcription factor may be c-Fos, FosB, Fra-1 and Fra-2. An ATF transcription factor may be ATF-1, ATF-2, ATF-3 and ATF-4. The transcription factor or fragment thereof may be labeled with a detectable label, for example, a radiolabel.

In the example of c-Jun and a Stat protein, the mutation may modulate the transcriptional cooperation between c-Jun and the protein at residues of said c-Jun at positions about 105 up to about 334, or about 105 to about 263.

The invention is also directed to polynucleotides encoding the various aforementioned Stat3 fragments, and the Stat3 mutants Stat3(L148A) (SEQ ID NO:30), Stat3(V151A) (SEQ ID NO:31), or Stat3(T346A, K348A, R350A) (SEQ ID NO:29). It is also directed to such polynucleotides which include a GST fusion sequence or an epitope tag.

The invention is further directed to cells transiently expressing a mutant Stat3 protein, the mutant Stat3 proteins as described above.

The invention is also directed to fragments of c-Jun 1–104 (SEQ ID NO:26) or 105–334 (SEQ ID NO:27), their polynucleotide sequences, as well as cells transiently expressing a mutant c-Jun fragment as described above.

The invention is also directed to methods for identifying a mutant Stat protein capable of modulating the transcriptional cooperation between a Stat protein and a transcription factor comprising the steps of:

(a) providing a transformed cell line;
(b) transfecting the transformed cell line with a Stat mutant suspected of interfering with the interaction between said Stat and a transcription factor;
(c) examining the transfected cell line for evidence of alteration of transformation in contrast to said cell line transfected with the wild-type Stat; and
(d) identifying a mutant capable of modulating the transcriptional cooperation between a Stat protein and a transcription factor as one which alters the transformation of the cells.

For example, evidence of alteration of transformation may be a change in morphology on soft agar.

These and other aspects of the present invention will be better appreciated by reference to the following drawings and Detailed Description.

BRIEF DESCRIPTION OF THE DRAWINGS

FIG. 4 A–B. Site-directed mutagenesis in region 1 and region 2 of Stat3 molecule. (A) Sequence alignment of Stat proteins in region 1 and region 2. Five shadowed residues in Stat3 were changed to alanine individually. Three shadowed residues in region 2 were changed to alanines simultaneously. The Sequence identifiers for the stat amino acid residues are as follows: stat 3 amino acid residues 134–154 (SEQ ID NO: 32); stat 3 amino acid residues 342–354 (SEQ ID NO: 33); stat 1 amino acid residues 134–154 (Seq ID NO: 34); stat 1 amino acid residues 342–354 (SEQ ID NO: 35); stat 2 amino acid residues 134–154 (SEQ ID NO: 36); stat 2 amino acid residues 342–354 (SEQ ID NO: 37); stat 4 amino acid residues 134–154 (SEQ ID NO: 38); stat 4 amino acid residues 342–354 (SEQ ID NO: 39); stat 5a amino acid residues 134–154 (SEQ ID NO: 40); stat 5a amino acid residues 342–354 (SEQ ID NO: 41; stat 6 amino acid residues 135–154 (SEQ ID NO: 42); stat 6 amino acid residues 342–354 (SEQ ID NO: 43). (B) Three Stat3 mutants showed decreased c-Jun binding property. L148A and V151A mutants (lanes 5 and 6) demonstrated a weaker c-Jun binding. TKR mutant (lane 12) in region 2 lost the c-Jun binding. WT, wild-type GST-Stat3 (130–358).

DETAILED DESCRIPTION OF THE INVENTION

Figure 1:
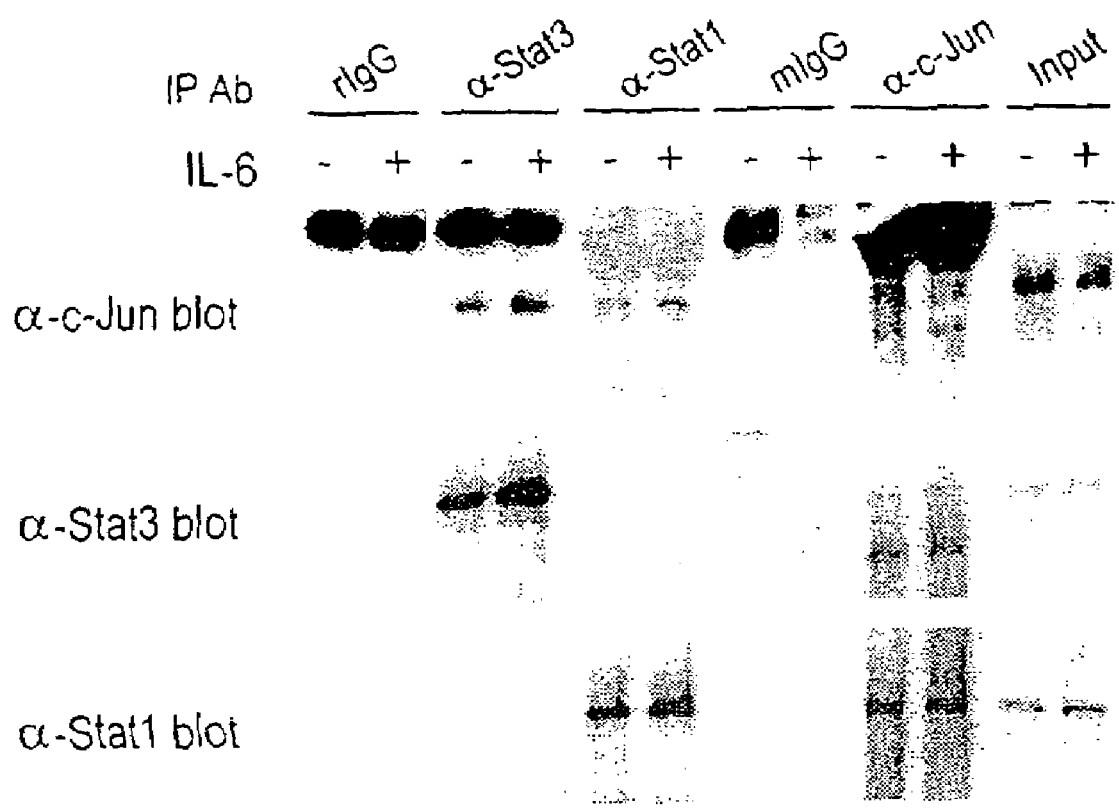
FIG. 1. Stat1 and Stat3 interact with c-Jun in vivo. Nuclear extracts (300 mg) from IL-6-treated or untreated HepG2 cells were immunoprecipitated with antibodies indicated, and the immunoprecipitates were then subjected to 10% SDS/PAGE, followed by Western blotting with antibodies indicated. rIgG, rabbit immunoglobulin and mIgG, mouse immunoglobulin (Santa Cruz) are used as controls for the Stats 1 and 3 or c-Jun immunoprecipitations respectively.

Transcriptional activation of mammalian genes is now universally regarded as requiring the cooperative effect of many proteins (8, 28). As will be noted in the description below, methods for locating required protein:protein interactions between two cooperating transcription factors by in vitro association of domains of each protein was employed to identify regions both in transcription factors and in Stat proteins which associate. In the Examples herein employing the transcription factor c-Jun and Stat1 and Stat3, and particular fragments and mutants thereof, it has been shown that particular regions of these molecules associate in order to activate transcription. The areas of interaction to provide the transcriptional cooperativity were identified by providing various fragments of the Stat protein, and identifying the protein regions necessary for activity. Mutations in these regions which block the protein: protein interaction and thus prevent cooperative transcriptional activation confirm the need for such regions for cooperativity. The discovery of particular regions containing interaction sites between these proteins, as well as a contact sites between c-Jun and Stat3 within the DNA binding domain, was a surprise. The Stat DNA binding domain is fairly large compared to other such domains and presents surfaces away from the single surface that interacts with DNA.

These findings enabled the development of new methods for identifying agents which modulate these interactions. Such interactions on a cellular basis are responsible for numerous downstream cellular functions, including cellular transformation, and as will be seen below, one utility of the methods herein is for the identification of potentially useful pharmacologically active agents which interfere with transformation and the development of a cellular dysproliferative state. Such methods may be performed in cell-free and cell-based systems. The methods herein also may be used in identifying additional mutants, of which such mutant proteins or fragments thereof if transfected or otherwise introduced into transformed cells, interfere with the transcriptional cooperation among the endogenous transcription factors and modulate transformation. A small molecule identified using the methods of the invention as interfering with cooperation may be used in the treatment of dysproliferative diseases, including but not limited to cancer and psoriasis. Such agents have utility both in the prophylaxis or prevention of the development of transformation in cells that may have a propensity for such a condition, and in the inhibition or treatment of cells that have undergone transformation.

The methods of the invention are broadly divided into a cell-free system in which cooperativity and binding of the proteins via fragments of mutants containing the sites of cooperativity or lacking them is monitored by conventional protein biochemical methods, and agents capable of promoting or dissociating these interactions are detected. In a second set of methods, a cell-based system which may be induced to express a particular protein or phenotype of interest by way of an endogenous gene or transfected reported gene, may transfected with the transcription factor and a Stat protein, at least one of the foregoing which is a mutant, and the inducibility of the reporter gene in the presence or absence of an agent suspected of modulating the cooperative activity between the proteins is determined on a functional level. In the foregoing example, a cell may already express a particular wild-type or mutant proteins that cooperates in transcriptional activation, and its mutant partner is introduced. Various methods for identifying the expression of the reporter gene, as well as other cellular manifestations of gene activation, may be monitored to determine activity. In both of the foregoing methods, the introduced proteins may be tagged with a detectable label to facilitate identification. As used in the methods herein, the term reporter gene refers to a gene whose transcriptional activation maybe monitored by measuring the activation of the gene. It may be a specifically constructed gene with a reporter segment that is readily detectable, or an endogenous gene whose activation may be monitored.

In a further method, the ability of mutant factors to interfere with the transcriptional cooperativity of wild-type factors is assessed by co-transfecting a cell with the wild-type and mutant factors, and in comparison with the wild-type cells, the effect of the mutant factor on transcription is determined. In another method, a transformed cell line is transfected with the mutant or fragment molecules described herein, and their effects on transformation is monitored.

The transcription factors and Stat proteins described herein may be derived from any species, including animals, plant, protist and prokaryotes. Animals include human, mammalian such as rodent including mouse, non-mammalian animals, and proteins of other multicellular animals. Plant proteins are also embraced herein as well as bacterial, fungal, protistan, and other sources. The cellular expression of these proteins, or introduction thereinto, may be of a cell of the same or different species or even kingdom than the protein; for example, a human protein may be expressed by a fungal cell. The invention is not limited to the source of these proteins nor the particular expression systems in which they are used.

The first method of the invention provides a means for identifying an agent capable of modulating the interaction between a transcription factor and a Stat protein. The methods are based upon the interaction between particular regions of the Stat protein, such as Stat1 and Stat3, and particular regions of transcription factors such as c-Jun, as identified by the inventors herein and described in the Examples below. The method employs a transcription factor or a fragment thereof. Examples of transcription factors include members of the JUN, the FOS, or the ATF families of transcription factors. For example, a JUN transcription factor may be c-Jun, JunB and JunD. A FOS transcription factor may be c-Fos, FosB, Fra-1 and Fra-2. An ATF transcription factor may be ATF-1, ATF-2, ATF-3 and ATF-4. Fragments of the transcription factor may also be used, as it has been found herein that the COOH-terminal portion includes the Stat binding region. Further, the fragment may comprise the bZIP region of the transcription factor. In the example of c-Jun, fragments may comprises the region of about residue 105 to about residue 334 of c-Jun, and more particularly, the region of about residue 105 to about residue 263 of c-Jun.

Preparation of the fragments of the aforementioned transcription factors may be performed follow standard procedures known to the skilled artisan. For example, deletions of portions of the wild-type c-Jun protein may be performed by in vitro translation of PCR products encoding corresponding portions of the c-Jun protein. Furthermore, the transcription factor fragment may also be a mutant, i.e., contain one or more altered, added or deleted amino acids as compared to the corresponding fragment of the wild-type protein.

The following c-Jun fragments described herein were prepared: residues 1-104 of c-Jun (SEQ ID NO:26), and residues 105–334 of c-Jun (SEQ ID NO:27).

To facilitate the identification of the interaction of the transcription factor with a Stat protein or fragment, the transcription factor or fragment thereof may be labeled with a detectable label, for example, a radiolabel. Examples of radiolabels include $^{35}S$, etc. To label the aforementioned fragment of c-Jun, a method such as in vitro translation employing $^{35}S$-labeled methionine may be used.

The method further includes a fragment of a Stat protein, the Stat proteins including but not limited to Stat1, Stat2, Stat3, Stat4, Stat5 and Stat6. The Stat protein fragments comprises a region within from about residue 107 to about residue 377 of Stat3 and the corresponding positions in the other related Stat proteins. This region has been found by the inventors herein to contain at least one binding site for the transcription factor. Such fragments may comprise the coiled-coil domain of said Stat protein and the first three β-strands of the DNA-binding domain of said Stat protein. By way of the example of Stat3, examples of suitable fragments include (1) the region comprising about residue 107 to about residue 358, (2) the region comprising about residue 130 to about residue 358, (3) the region comprising about residue 155 to about residue 377, (4) the region comprising about residue 193 to about residue 377, (5) the region comprising about residue 249 to about residue 377, and (6) the region comprising about residue 282 to about residue 377. The corresponding fragments in other Stat proteins are also embraced by the invention. The fragments may further be mutant forms, i.e., have one or more altered, added or deleted amino acids as compared to a corresponding fragment of the wild-type Stat protein.

The Stat protein or fragment may be labeled with a detectable label, such as a GST fusion sequence or an epitope tag, or a radiolabel, such that the Stat protein or fragment may be easily isolated, detected or otherwise quantitated in the assay. Methods for such labeling, including in vitro translation to introduce a radiolabel into the protein, or expression of the protein with an epitope tag such as FLAG, or a GST sequence, are methods known to one of skill in the art.

The following table sets forth the sequences of exemplary suitable fragments, which may be prepared as GST fusion products.

| | |
|---|---|
| Residues 1–154 of Stat 3 | SEQ ID NO: 8 |
| Residues 107–377 of Stat 3 | SEQ ID NO: 9 |
| Residues 107–358 of Stat 3 | SEQ ID NO: 14 |
| Residues 107–342 of Stat 3 | SEQ ID NO: 15 |
| Residues 107–282 of Stat 3 | SEQ ID NO: 16 |
| Residues 107–249 of Stat 3 | SEQ ID NO: 17 |
| Residues 130–358 of Stat 3 | SEQ ID NO: 18 |
| Residues 130–342 of Stat 3 | SEQ ID NO: 19 |
| Residues 155–282 of Stat 3 | SEQ ID NO: 20 |
| Residues 155–249 of Stat 3 | SEQ ID NO: 21 |
| Residues 155–377 of Stat 3 | SEQ ID NO: 22 |
| Residues 193–377 of Stat 3 | SEQ ID NO: 23 |
| Residues 249–377 of Stat 3 | SEQ ID NO: 24 |
| Residues 282–377 of Stat 3 | SEQ ID NO: 25 |

In the practice of the method, a mixture of the aforementioned Stat protein fragment and the transcription factor or fragment thereof are incubated under the appropriate conditions to promote the interaction and binding of the two proteins through the aforementioned interacting sites. Such studies may be performed using a cellular extract, for example, prepared from lysed HepG2 cells. Such assays have been described previously (43). A mixture under the same conditions also in the presence of an agent to be evaluated for its modulating properties on the interaction. Such agents may promote or disrupt, partially or completely, the interaction. Such agents may include small molecules, proteins, including peptides or fragments of a Stat protein or a transcription factor, including those particular molecules described herein, as well as other fragments, mutants, mutant fragments, etc.

To detect the effect of the agent on the interaction, the association between the Stat protein or fragment and the transcription factor or fragment is determined. Such methods as co-immunoprecipitation, a GST protein association assay, and the yeast 2-hybrid system, may be used to detect the interaction. To determine the effect of the agent on the interaction, the level of interaction in the presence and absence of the agent are compared, to arrive at a determination of whether the agent is capable of promoting or interfering with the association, and to what extent. Agents capable of promoting the association result in an increased level of associated transcription factor and Stat protein complexes; agents that interfere with the association result in a reduced or absence of associated complexes.

As noted above, in the example of Stat3, the agent may modulate the interaction between the transcription factor and the Stat3 protein at residues of Stat3 protein identified as the sites of interaction, namely, residues 130–154, or residues 343–358. Interactions at either or both sites may be modulated. On c-Jun, the interaction between c-Jun and a Stat protein may involve about residue 105 up to about 334 of c-Jun, and more particularly, about 105 to about 263.

The foregoing method may be adapted for high-throughput screening.

In another method of the present invention, the ability of an agent to modulate the interaction between a transcription factor and a Stat protein may be determined in a cellular system, in which transcriptional cooperativity between the appropriate portions of the transcription factor and the Stat protein are determined by their effect on gene transcription. In this method, the readout is the transcription of an endogenous gene or downstream effect of activation of a particular gene, or detection of the activation of a reporter gene introduced into a cell. In the practice of the method, first a transfected cell bearing a Stat-inducible reporter gene or a Stat-inducible endogenous gene is used as the eventual readout of the assay. Examples of such cells and reporter genes useful for this method include but are not limited to a luciferase reporter plasmid constructed by releasing the $\alpha_2$-macroglobulin promoter fragment from $\alpha_2$-macroglobulin-TK-CAT-WT (see reference 30) and inserting it into a vector pTATA that has the TATA box of the thymidylate kinase gene. Another example is a luciferase reporter gene containing 3 Ly6E sites (see reference 39). A further example is a pCMV β-gal construct. Examples of cells in which an endogenous gene or activity may be monitored for effects of transcriptional cooperativity include but are not limited to cyclin D1, Bcl-xL and c-Myc. As will be noted below, in the procedure, such cells are exposed to an activator to induce the expression of the detectable gene; for example, IL-6 or IFN-γ.

The above-mentioned cells have introduced thereinto a transcriptionally cooperative combination of a wild-type Stat protein or a mutant Stat protein, and a wild-type transcription factor or a mutant transcription factor. For an operable assay, these proteins cooperate to induce gene transcription. At least one of the introduced Stat protein or transcription factor is a mutant; both may be mutants. For example, the wild-type Stat protein may be Stat1, Stat2, Stat3, Stat4, Stat5 or Stat6. A mutant Stat protein may include the coiled-coil domain of said Stat protein and the first three-strands of the DNA-binding domain of said Stat protein. At least one mutation may be present within residues 130–134 or within 343–358.

In the practice of the method, the cells transfected with or expressing the foregoing cooperating proteins is exposed to an agent suspected of modulating the cooperative interaction. Such agents may be added to the cells; another agent may be a protein or fragment thereof which must be introduced into said cell by transfection or delivery. The expression of the agent within the cell may be induced by the addition of an agent which induces te expression of the agent. Following or concurrent with exposure of the cooperative protein to the candidate agent, the cells are treated to induce expression of the reporter gene or endogenous gene to provide the readout of modulation of cooperativity. The difference in the extent of expression of the reporter gene in the presence and absence of said agent permits the identification of an agent capable of modulating the interaction.

Selection of Stat proteins and transcription factors is as described hereinabove. Suitable agents are expected to interfere with or promote the interaction between the transcription factor and the Stat protein at the sites identified herein; for example, in Stat3 protein, at residues 130–154, residues 343–358, or both.

Examples of mutant Stat proteins include those homologous to Stat3 mutants having at least one mutation in a region of the native Stat3 sequence at positions 130–154, residues 343–358, and the combination thereof. Examples of such mutants include but are not limited to Stat3(L148A) (SEQ ID NO:30), Stat3(VlSlA) (SEQ ID NO:31), and Stat3(T346A, K348A, R350A) (SEQ ID NO:29). These mutants are prepared using conventional means, such as site-directed mutagenesis. The Stat protein or mutant thereof used in this method may also be labeled with a detectable label, such as a GST fusion sequence or an epitope tag. This facilitates additional confirmation of modulation of cooperativity by the means described for the previous method.

The selections for the transcription factor are those described above. In the example of c-Jun, the agent may modulates the transcriptional cooperation between said transcription factor and a Stat protein at residues of said c-Jun protein at residues about 105 up to about 334, and between about 105 and about 263.

Agents capable of modulating cooperativity of the transcription factor and Stat to interfere with or promote gene transcription may be a small molecule which interacts with either or both proteins at their sites of interaction, as discovered by the inventors herein, or the agent may itself be a modified transcription factor, Stat protein, fragment or mutant thereof, which interferes with or competes with the wild-type protein for binding, and, for example, has a defective DNA binding site and thus disrupts gene transcription. The invention is not limited to any particular mechanism by which the agents of the invention interfere with or promote transcriptional cooperativity. Candidate agents include the aforementioned segments of the respective proteins which comprise the binding sites, in addition to small molecules capable of interfering or promoting.

In the instance where the agent is a modified protein, fragment or mutant thereof, the test system may comprise the wild-type form of the protein, such that the effect of the modified protein in the presence of the wild-type protein may be evaluated. For example, the foregoing mutant Stat3 molecules may be evaluated as candidate modulators by transfecting these into cells bearing the wild-type Stat3 molecule. As will be noted in the examples below, mutations in two particular regions of Stat3, within residues 130–154 and 342–358 (referred to as regions 1 and 2, respectively), block the cooperation between Stat3 and c-Jun. These inhibitors and their related proteins and peptides, are candidate inhibitors that maybe used therapeutically for interfering with transcriptional cooperativity and useful in the prophylaxis or treatment of cellular transformation.

For example, the following mutants of Stat3 are useful for the aforementioned purposes: Stat3(L148A) (SEQ ID NO:30), Stat3(V151A) (SEQ ID NO:31), and Stat3(T346A, K348A, R350A) (SEQ ID NO:29). Other mutants, as well as fragments of such mutants, that inhibit cooperative transcription are also embraced by the invention.

As there is significant homology between the various Stat proteins, the exemplary mutants and regions of the Stat3 molecule described above have their corresponding mutations and regions in the other Stat molecules. The invention embraces the corresponding mutations in other Stat molecules, which will be readily identified by a skilled artisan in comparing the sequences. Such correspondence also extend to Stat molecules of other species, including among and between kingdoms.

The agents which interfere with cooperativity of the transcription factor and the Stat protein may also interfere with the particular regions of the transcription factor that interact with the Stat protein. For example, mutant or mutant fragments of c-Jun with mutations in the region encompassing about residue 105 up to about residue 334, and more particularly, about residue 105 to about residue 263, provide proteins capable of interfering with c-Jun-Stat interactions, and thus such mutants are candidate modulators of cooperative interactions and transcription. As noted above, c-Jun is a non-limiting example of a transcription factor; corresponding or homologous regions of the members of other transcription factor families, among and between species, are embraced herein.

The present invention is also directed to a method for identifying mutant transcription factors, mutant Stat proteins, or both, wherein the mutant is capable of modulating the transcriptional cooperation between the transcription factor and a Stat protein. The method is carried out by the steps of:

(a) providing a transiently transfected cell bearing a Stat-inducible reporter gene;

(b) introducing into the cell a wild-type Stat protein, fragment or mutant thereof; and a wild-type transcription factor, fragment or mutant thereof, wherein at least one of the introduced Stat protein or transcription factor is mutant or a fragment;

(c) inducing the expression of the reporter gene;

(e) determining the extent of expression of the reporter gene compared to said extent in a cell having a wild-type form of at least one of the mutant transcription factor or the mutant Stat protein; and (f) identifying a mutant as one capable of modulating the interaction as one able to alter the expression of the reporter gene.

Examples of Stat proteins and their fragments suitable for use in the foregoing method are those as described hereinabove, for example, a Stat protein or mutant which comprises the coiled-coil domain of the Stat protein and the first three β-strands of the DNA-binding domain of the Stat protein. The Stat protein may be Stat11, Stat2, Stat3, Stat4, Stat5 or Stat6. In the example of Stat3, a mutation may be detected by the foregoing method that modulates the transcriptional cooperation between the transcription factor and the Stat3 protein at Stat3 residues about 130 to about 154, residues about 343 to about 358, or both. At least one mutation in a region of the native Stat3 sequence may be present at positions between about residues 130 and about 154, residues about 343 to about 358, and the combination thereof. Non-limiting examples of Stat mutants detectable by the foregoing method include Stat3(L148A) (SEQ ID NO:30), Stat3(VlSlA) (SEQ ID NO:31), and Stat3(T346A, K348A, R350A) (SEQ ID NO:29). As noted above, the corresponding regions and positions in the other Stat molecules are embraced herein, and the skilled artisan will be cognizant of the homologies among the proteins and identifying the corresponding regions and positions.

Examples of transcription factors are those as described hereinabove, including the members JUN, the FOS, and the ATF families of transcription factors. By way of non-limiting example, mutant or fragments of transcription factor and said Stat3 protein comprise residues of said c-Jun at positions about 105 up to about 334, or about 105 to about 263.

The invention is also directed to the Stat fragments and mutants described hereinabove. Methods known to one of ordinary skill in the art may be used to prepare these proteins, for example, as described in the Examples herein. These fragments residues 1–154 of Stat3 (SEQ ID NO:8), residues 107–377 of Stat3 (SEQ ID NO:9), residues 107–358 of Stat3 (SEQ ID NO:14), residues 107–342 of Stat3 (SEQ ID NO:15), residues 107–282 of Stat3 (SEQ ID NO:16), residues 107–249 of Stat3 (SEQ ID NO:17), residues 130–358 of Stat3 (SEQ ID NO:18), residues 130–342 of Stat3 (SEQ ID NO:19), residues 155–282 of Stat3 (SEQ ID NO:20), residues 155–249 of Stat3 (SEQ ID NO:21), residues 155–377 of Stat3 (SEQ ID NO:22), residues 193–377 of Stat3 (SEQ ID NO:23); residues 249–377 of Stat3 (SEQ ID NO:24); residues 282–377 of Stat3 (SEQ ID NO:25), residues 1–154 of Stat1 (SEQ ID NO:11), residues 107–374 of Stat1 (SEQ ID NO:12), and residues 375–750 of Stat1 (SEQ ID NO:13). The mutant stat proteins include Stat3(L148A) (SEQ ID NO:30), Stat3(V151A) (SEQ ID NO:31), or Stat3(T346A, K348A, R350A) (SEQ ID NO:29). These fragment may include a GST fusion sequence or an epitope tag.

The invention is also directed to polynucleotide sequences encoding the Stat3 fragments and mutants described above. The aforementioned nucleotide sequences may also comprise a GST fusion sequence or an epitope tag. The polynucleotides may be prepared using well-known procedures. Accordingly, there may be employed conventional molecular biology, microbiology, and recombinant DNA techniques within the skill of the art for the preparation of the proteins, protein fragments, mutants, polynucleotides, and cells of the invention. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

The invention is also directed to cells transiently or stably transfected with a mutant Stat3 protein as described hereinabove.

The invention is further directed to Stat-interaction fragments of c-Jun, for example, 1–104 (SEQ ID NO:26) or 105–334 (SEQ ID NO:27), their corresponding polynucleotide sequences, as well as to cells transiently or stably expressing the foregoing fragments. These fragments, polynucleotides and cells may be prepared following standard techniques such as those described or referred to herein.

As noted above, the foregoing method for identifying agents capable of modulating the physical or transcriptional cooperativity of the transcription factor and Stat protein are those capable of modulating cellular transformation. Agents which interfere with the cooperativity inhibit cellular transformation.

A further aspect of the present invention is a method for identifying a mutant Stat protein capable of modulating the transcriptional cooperation between a Stat protein and a transcription factor which utilizes a transformed cell line as the assay system, and modulation of transformation as the assay readout. The method comprises the steps of:

(a) providing a transformed cell line;
(b) transfecting the cell line with a Stat mutant suspected of interfering with the interaction between the Stat protein and a transcription factor;
(c) examining said cell line for evidence of alteration of transformation in contrast to said cell line transfected with the wild-type Stat;
(d) identifying a mutant capable of modulating the transcriptional cooperation between a Stat protein and a transcription factor as one which alters the transformation of the cells.

Transformed cell lines useful for the foregoing method include human fibroblasts. Evidence of alteration of transformation may be detected by, for example, a change in morphology on soft agar.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Stat3 and Stat1 Interact with c-Jun in Vivo

Cell culture and antibodies. Human HepG2 cells were maintained in Dulbecco's modified Eagle's medium (DMEM) supplemented with 15% fetal bovine serum (HyClone). Human 293T cells were maintained in DMEM supplemented with 10% fetal bovine serum. Anti-Stat3 serum and anti-Stat1 serum were raised in rabbit as previously described (32, 33, 44, 45) and diluted 1:1000 for Western blotting, 1:10 for supershifting DNA-protein complexes in electrophoretic mobility shift assays (EMSA). Monoclonal c-Jun antibody (Santa Cruz) was diluted 1:500 for Western blotting. Anti-phospho Stat3 (Tyr 705) antibody (New England Biolabs) was used at a 1:5000 dilution and anti-phospho Stat3 (Ser 727) antibody (New England Biolabs) was used at a 1:1000 dilution for Western blotting. Anti-FLAG monoclonal antibody (Kodak/IBI) was used at a 1:1000 dilution for Western blotting and at a 1:10 dilution for supershifting DNA-protein complexes. Human IL-6 was purchased from Boehringer Mannheim and was used at a concentration of 5 ng/ml. The recombinant soluble form of the human IL-6 receptor was purchased from R&D Systems and was used at a concentration of 5 ng/ml. IFN-γ was a gift of Amgen Inc. and was used at 5 ng/ml for 30 min.

Plasmid constructions. GST-fusion constructs with the indicated Stat3 fragments were generated by PCR using primers containing 5' BamHI sites and 3' NotI sites. Amplified products were digested with appropriate enzymes and cloned into pGEX-5X-1 (Pharmacia). Construction of the expression vector pRcCMV (Invitrogen) containing Stat1 and Stat3 was as previously described (39). The expression vector of c-Jun, pRSV-Jun, was a gift from Daniel Besser (The Rockefeller University). The luciferase reporter plasmid was constructed by releasing the $\alpha_2$-macroglobulin promoter fragment from $_2$-macroglobulin-TK-CAT-WT (a gift from Daniel Nathans, John Hopkins University School of Medicine) (30) and inserting it into vector pTATA (a gift from Daniel Besser) that has the TATA box of the TK (thymidine kinase) gene. The luciferase reporter gene containing 3 Ly6E sites was previously described (39). pCMV-βgal construct was purchased from Invitrogen.

Glutathione S-transferase (GST)-fusion protein association assay. Preparation of GST fusion proteins was carried out by induction of *Escherichia coli* containing the fusion vector at 30° C. with 1 mM IPTG. Following lysis by sonication, GST proteins were purified on glutathione-Sepharose beads (Pharmacia) and washed extensively with phosphate-buffered saline. For in vitro translation of proteins, full-length c-Jun cDNA was used for program coupled transcription and translation reactions in the presence of $^{35}$S-labeled methionine (DuPont/NEN) according to the manufacturer's directions (TNT; Promega). GST protein association assays with translation products or HepG2 extracts were carried as previously described (43). After washing, the resulting binding complexes were eluted in SDS-gel loading buffer and separated by 10% SDS/PAGE.

Transfection. Transient transfections were done on 24-well plates with $2.5 \times 10^5$ cells per well using the calcium phosphate method as instructed by the manufacturer (GIBCO/BRL). Total amount of DNA transfected was brought up to 2 mg per well using sonicated salmon sperm DNA. Twenty four hours after transfection, cells were treated with either IL-6 or IFN-γ for 6 hr or left untreated. Luciferase assays were performed according to the manufacturer's directions (Promega) and β-galactosidase (β-gal) assays were done as previously described (2). All results shown are luciferase activities normalized against the internal control β-gal activity. Each sample was performed in triplicate in a single experiment and repeated in three different experiments with similar results.

Cell extracts and immunoblots. Whole-cell lysates and nuclear extracts were prepared as described previously (35). Immunoprecipitation and Western blots were carried out by standard methods (2).

Site-directed mutagenesis. The QuickChange site-directed mutagenesis method (Promega) was used to introduce mutations into Stat3.

Primer 5'CACCCAACAGCCGCCGTA GCAACAGAGAAGCAGVAGATG 3' (SEQ ID NO:1) was used to create the V137A mutant, 5' GCCGTAGTGACA-GAGAAGGCACAGATGTTGGAGCAGCAT 3' (SEQ ID NO:2) was used to create the Q141A mutant, 5' GCCG-TAGTGACAGAG AAGCAGCAGATG GCAGAGCAGCATCTTCAGGATGTC 3' (SEQ ID NO:3) was used to create the L144A mutant, 5' ATGTTGGAG-CAGCATGCTCAGGATGTCCGGAAGC 3' (SEQ ID NO:4) was used to create the L148A mutant, 5' GCAG-CATCTTCAGGATGCACGGAAGCGAGTGCAGG 3' (SEQ ID NO:5) was used to create the V151A mutant and 5' CAACTCAGGAAATTTGACCAGCAACGCGAC TGCCGTGGCAAACTGGACAC CAGTCTTG 3' (SEQ ID NO:6) was used to create the TKR mutant.

Electrophoretic mobility shift assay (EMSA). Nuclear extracts (~2 to 3 mg protein) from IL-6-treated 293T cells transfected with FLAG-tagged Stat3 constructs were incubated with 1 ng of $^{32}$P-labeled M67 probe (38) for 20 min at room temperature. 2 to 3 mg of nuclear extracts from HepG2 cells untreated and treated with either IL-6 or IFN-γ were incubated with $^{32}$P-labeled α$_2$MGAS probe containing the GAS element in the α$_2$M-macroglobulin enhancer (5' AATCCTTCTGGGAATTC 3' (SEQ ID NO: 7)). The protein-DNA complexes were analyzed by EMSA as previously described (13).

In preliminary experiments using yeast 2-hybrid assays, detection of interactions between Stat1 and 3 with c-Jun was performed. Weak interactions with amino terminal portions of Stat3 but not Stat1 were observed (data not shown). IL-6 treatment of cells at low doses favors activation of Stat3 and at higher doses also leads to activation of Stat1 29, 45). Therefore, whether co-immunoprecipitation of c-Jun with either Stat1 or Stat3 could be observed using nuclear extracts from IL-6 treated and untreated HepG2 cells was tested. In both treated and untreated cell extracts, both Stat1 and 3 could be co-precipitated by c-Jun antibody and Stat antibodies also precipitated c-Jun, while control antibodies did not co-immunoprecipitate c-Jun, Stat1 or Stat3 (FIG. 1). Although no definitive conclusions can be drawn about Stat-c-Jun affinities from such experiments, or from the earlier yeast 2-hybrid results (30), it encouraged the search for sites of protein:protein interactions between Stats and c-Jun. Since an interaction between an IRF family protein, p48, and Stat1 was previously demonstrated to lie in a region between 150–200 amino acids from the N-terminus (in the coil:coil region of the Stat structure), it was anticipated that this region might also contain binding sites for other nuclear proteins (19).

EXAMPLE 2

Mapping the c-Jun:Stat Binding Domains

Figure 2A:
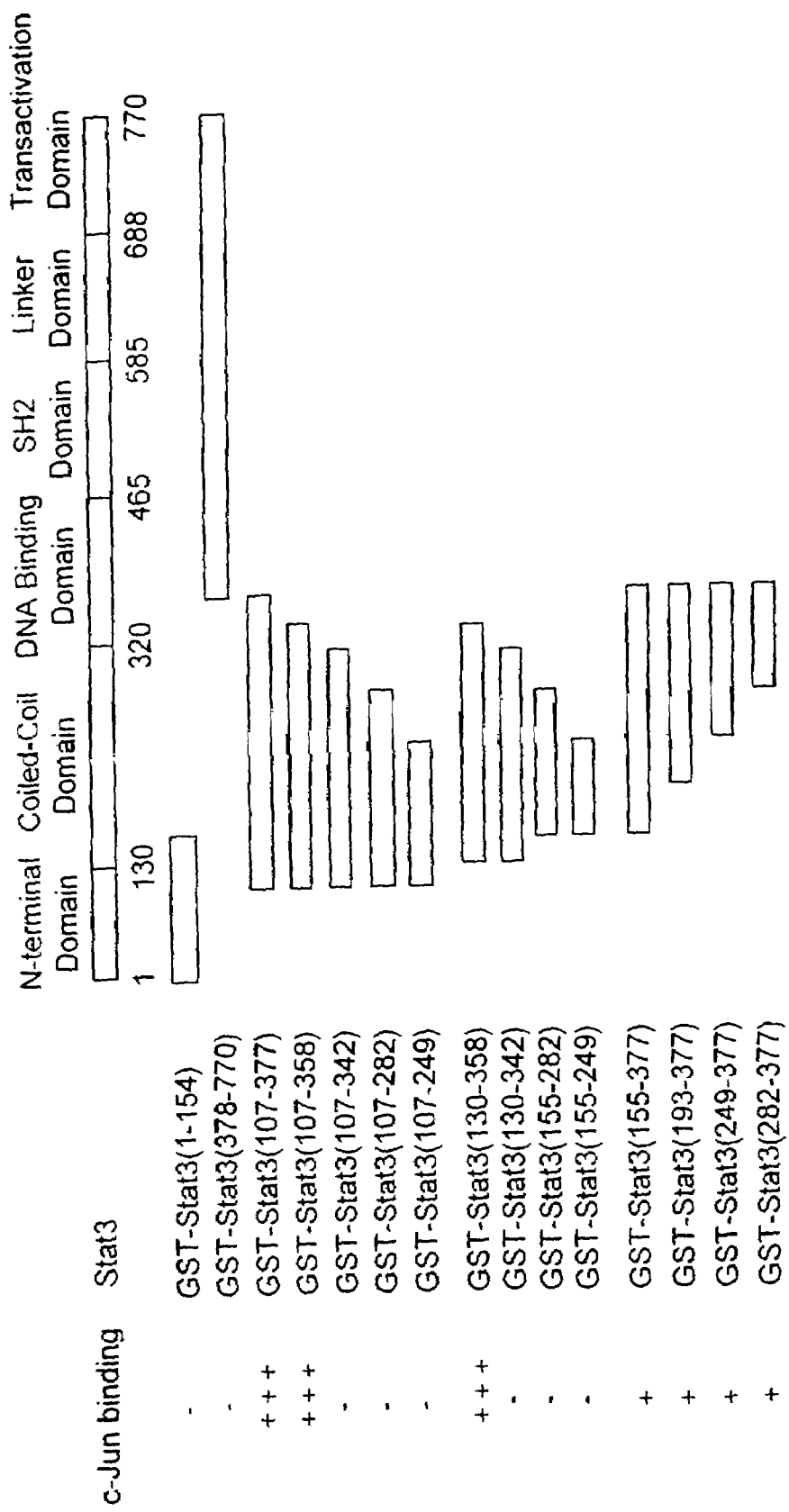
FIG. 2 A–D. Mapping of the regions in Stat1 and 3 that interact with in vitro translated c-Jun using GST pull-down assays. (A) A schematic diagram of the structure domains of Stat3 and a summary of interaction between c-Jun and various GST-Stat3 fusion fragments. (B) c-Jun interacts with GST-Stat3 (107–377). (C) Mapping of the minimal c-Jun interactive region in Stat3. Equivalent amounts of each GST-Stat3 fusion proteins attached to glutathione Sepharose beads were incubated with in vitro translated full-length c-Jun label with $^{35}$S-methionine. The bound proteins were analyzed by 10% SDS-PAGE and exposed to radiograph. (D) Endogenous c-Jun interacts with Stat3 GST-fusion proteins. HepG2 cell extracts were incubated with GST-Stat3 fusion proteins bound on glutathione Sepharose beads. The precipitates were analyzed by 10% SDS-PAGE and blotted using a-c-Jun antibody.
Figure 2B:
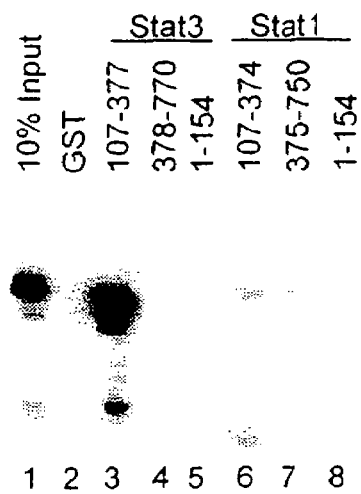

The domain boundaries of Stat1 or 3 in FIG. 2A are marked according to recent crystallographic study of Stat3b core dimer on DNA (4). These domains are virtually identical in both Stat3 (4) and in Stat1 (9) for which the crystallographic co-ordinates are known. In order to define potentially interactive domains of Stat1 or 3 with c-Jun, GST fusion proteins containing three different regions of Stat3 (1–154 [SEQ ID NO:8], 107–377 [SEQ ID NO:9] and 378–770 [SEQ ID NO:10]) and of Stat1 (1–154 [SEQ ID NO:11], 107–374 [SEQ ID NO:12], 375–750 [SEQ ID NO:13]) were prepared and coupled to Sepharose beads. Full-length $^{35}$S labeled c-Jun produced by in vitro translation was incubated with the different sections of Stats and the bound proteins were analyzed by gel electrophoresis and autoradiography (approximately equal amounts of GST fusion proteins were used in each fragment assay; FIG. 2B). The GST-Stat3 (107–377) fusion protein [SEQ ID NO:9] interacted strongly with c-Jun (FIG. 2B, lane 3) while the NH2 terminal (1–154) and COOH terminal (378–770) Stat3 fusion fragments [SEQ ID NO:8 and 10, respectively] bound very little c-Jun (FIG. 2B, lanes 4 and 5). Residues 107 to 377 of Stat3 include the entire coiled-coil domain evident in the crystal structure and 57 amino acid residues of the DNA binding domain. In contrast, no fragment of Stat1 tested bound strongly to c-Jun in several attempts with this assay although weak interactions were observed (FIG. 2B, lanes 6–8). These very clear results contrast with the co-immunoprecipitation experiments of FIG. 1. Perhaps the Stat1 (107–374) fragment [SEQ ID NO:12] does not fold correctly to present interaction sites or some additional protein is required for Stat1:c-Jun interaction.

Figure 2C:
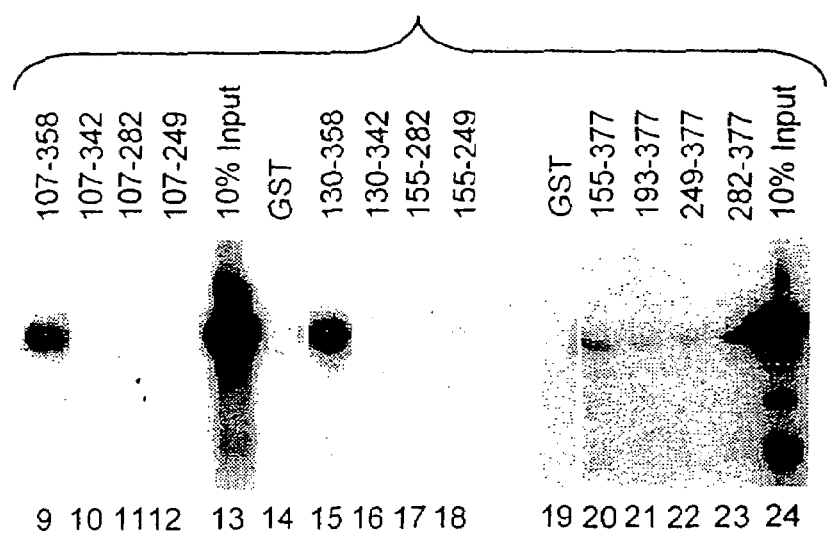

Further deletions from either or both ends of the Stat3 107–377 segment were generated and GST-fusion proteins were prepared to map the minimal region of Stat3 required for the observed in vitro c-Jun binding (FIGS. 2A and 2C). Equivalent amounts of each GST fusion protein bound to beads were again incubated with in vitro translated full-length c-Jun. Residues 130 to 358 of Stat3 [SEQ ID NO:18] were essential and sufficient for c-Jun binding (FIG. 2C, lane 15). Deletion of N-terminal residues up to residue 154 decreased c-Jun binding and deletion of C-terminal residues 343 to 358 abolished the c-Jun binding (FIG. 2C, lanes 20 and 16). Thus these two regions were candidates to contain residues involved in c-Jun binding.

Figure 2D:
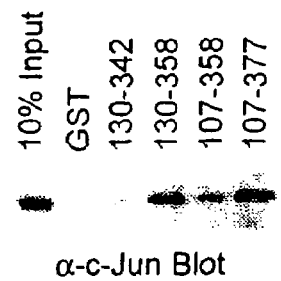

To determine whether the Stat3 fusion proteins could bind endogenous c-Jun from HepG2 whole cell extracts, three interacting Stat3 GST fusion fragments were incubated with HepG2 cell extracts. The protein was eluted from the Stat3-beads, separated by SDS-PAGE followed by immunoblotting with c-Jun antibody (FIG. 2D). Consistent with the results using in vitro synthesized c-Jun, the negative control GST-Stat 3 (130–342 [SEQ ID NO:19]), showed very weak c-Jun binding, but three other Stat3 fragments (130–358 [SEQ ID NO:18], 107–358 [SEQ ID NO:14], 107–377 [SEQ ID NO:9]) all reacted strongly with the c-Jun in the cell extracts.

EXAMPLE 3

Stat3 Interactive Region in c-Jun Lies Within Residues 105–334

Figure 3A:
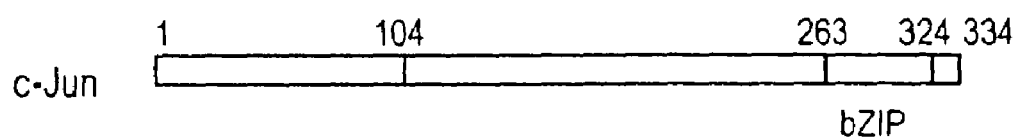
FIG. 3 A–B. Mapping of the Stat3 interactive region in c-Jun using GST pull-down assays. (A) Schematic diagram of the structure domains of c-Jun. The fragments of c-Jun that were in vitro translated were residues 1–104 and 105–334. (B) The fragment 105–334 of c-Jun is sufficient to bind to GST-Stat3 (107–377). bZIP, basic leucine zipper.
Figure 3B:
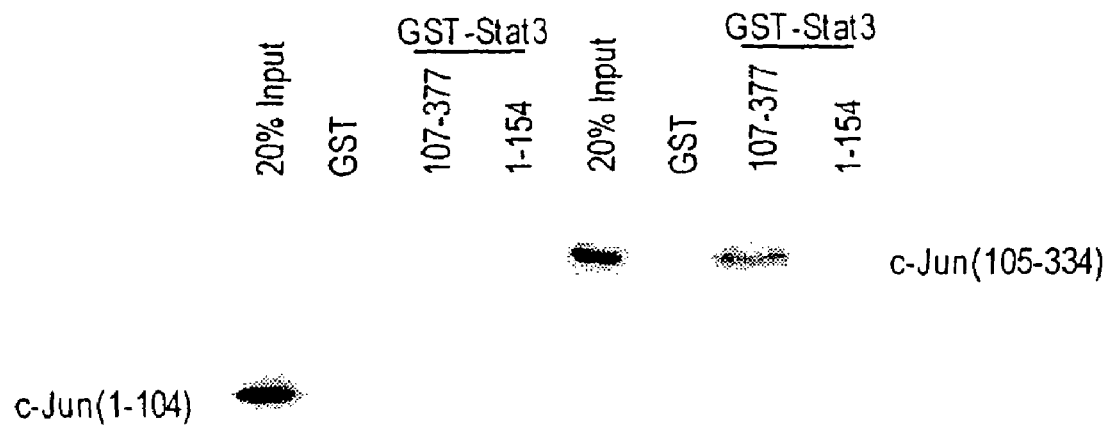

To define the Stat3 binding segment of c-Jun, the N-terminal region containing residues 1 to 104 [SEQ ID NO:26] and C-terminal region containing residues 105 to 334 of c-Jun [SEQ ID NO:27] were labeled with $^{35}$S by in vitro translation. These labeled products were incubated with the GST-Stat3 fragments containing either 107–377 [SEQ ID NO:9] or 1–154 [SEQ ID NO:8]. While the N-terminal region of c-Jun did not bind to GST-Stat3 (1–154), the C-terminal region of c-Jun was bound strongly to GST-Stat3 (107–377) (FIG. 3B). The C-terminal segment of c-Jun contains the bZIP region of c-Jun (263–324) that, in association with c-Fos and DNA, was studied crystallographically (16). Since the 263–324 region of c-Jun engages in dimerization and DNA binding, it is tempting to speculate that the 108–263 region of c-Jun contains residues that might contact Stat3 when the two proteins are bound simultaneously to DNA.

EXAMPLE 4

Site-Directed Mutagenesis in Two Regions of Stat3

Figure 5A:
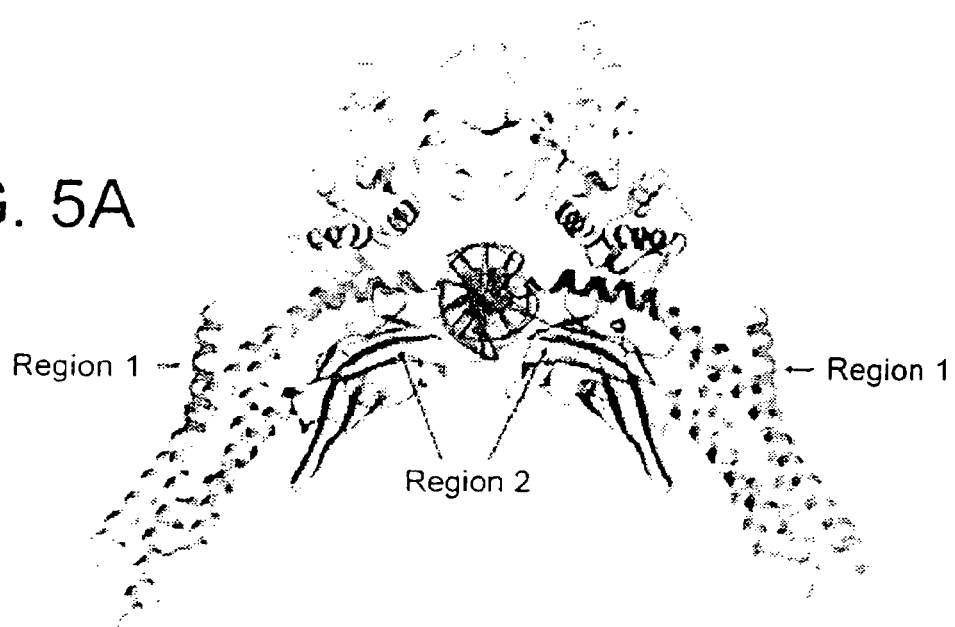
FIG. 5 A–C. Ribbon diagrams of regions 1 and 2 where site-directed mutagenesis was performed and the corresponding mutated residues in Stat1 molecule. (A) Two c-Jun interactive regions in Stat3 are shown in a ribbon diagram of the Stat1 core dimer on DNA. Region 1 is shown in magenta and region 2 is shown in purple. The coiled-coil domain is shown in green, DNA binding domain in red, linker domain in orange, SH2 domain in cyan. The tail segments are shown in green and in magenta. (B) Four corresponding mutated residues in region 1 of Stat3 are shown in a ribbon diagram of the coiled-coil domain (green) and DNA binding domain (red) of Stat1 monomer. M135 in Stat1, the corresponding residue of V137 in Stat3 is not included in the ribbon diagram. (C) Three corresponding mutated residues in region 2 of Stat3 are shown in a ribbon diagram of the DNA binding domain of Stat1 monomer with DNA.
Figure 5B:
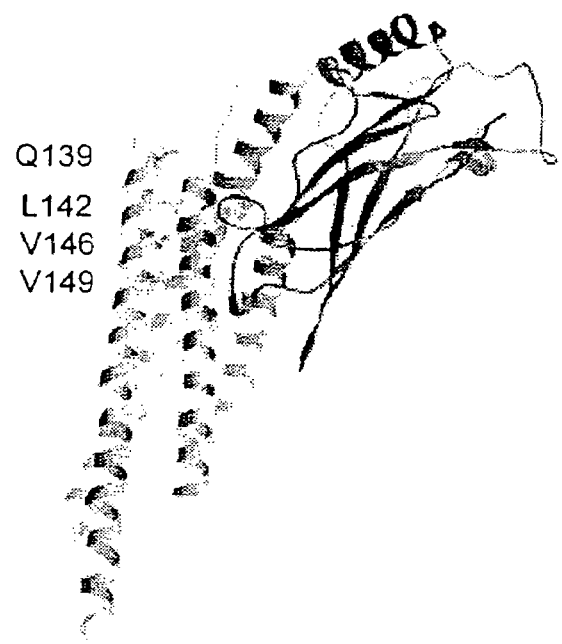
Figure 5C:
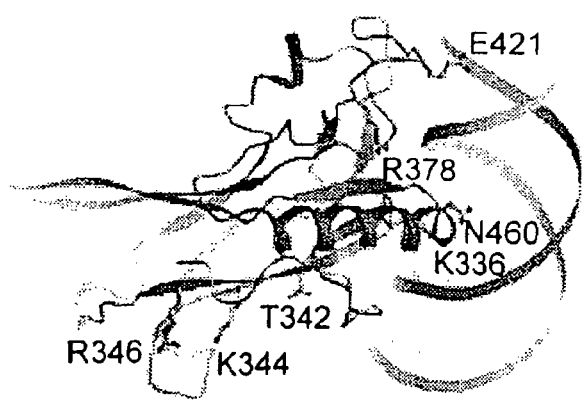

In order to identify specific residues of Stat3 that might be important for Stat3-c-Jun interaction, and guided by the deletion results showing Stat3 residues between 130 and 154 (region 1) and 342 to 358 (region 2) to be important in Stat3-c-Jun interaction (FIG. 2A), site-directed mutagenesis was performed in these two regions. Sequence alignment of seven mammalian Stat proteins reveals five conserved residues in region 1 (FIG. 4A). Each of the conserved residues was changed to alanine (FIG. 5B). Region 2 lies toward the NH2 terminal end of the structural domain that contains DNA contact residues; three conserved residues that do not make close contact with DNA were all changed to alanine (FIG. 4A, 5C).

Stat3 cDNAs encoding region 130 to 358 [SEQ ID NO:28] with the corresponding mutations were expressed as GST fusion proteins and tested for their binding ability to labeled c-Jun. Two mutants in region 1, L148A, and the other, V 151A, demonstrated a weaker binding of c-Jun. (FIG. 4B, lanes 5 and 6). The triple mutation (T346A, K348A, R350A) in region 2 virtually abolished c-Jun binding (FIG. 4B, lane 12). Thus it appeared that residues within the coiled-coil domain as well as within the first three b-strands of the DNA binding domain of Stat3 may be involved in the Stat3-c-Jun interaction. To evaluate the functional importance of the c-Jun-Stat 3 interactions indicated by these experiments, a transient transfection analysis was employed (FIG. 6). Stat1 was included in these experiments both to determine whether it could supplant Stat3 and as a closely related "control" protein.

EXAMPLE 5

Figure 6A:
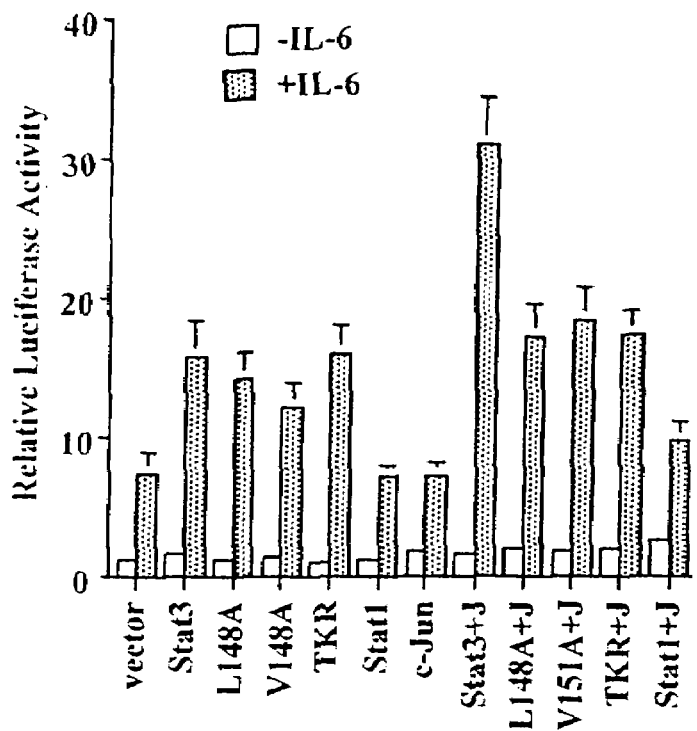
FIG. 6. Requirement of Stat3-c-Jun interaction for maximal activation of an IL-6-inducible $\alpha_2$-macroglobulin reporter gene containing both Stat3 and AP-1 binding sites. (A) Co-transfection of wild-type Stat3 and c-Jun boosted the IL-6 dependent response, while Stat1 and three non-interactive Stat3 mutants were ineffective with c-Jun in increasing the IL-6 dependent response. HepG2 cells were transfected with 0.5 mg of luciferase reporter, 0.2 mg of CMVbgal, 50 ng of Stat3 and 50 ng of c-Jun. Twenty four hours after transfection, cells were treated with 5 ng of IL-6 per ml for 6 hr and harvested for luciferase assay and β-gal assay. Results shown are the mean +/−standard deviation of 3 experiments. The luciferase activity was normalized against the internal control. β-gal activity and calculated as fold relative to the activity from cells transfected with the vector plasmid pRcCMV. (B) Stat1 was ineffective in cooperating with c-Jun to activate IL-6 induced transcriptional response. HepG2 cells were co-transfected with 0.5 mg of $\alpha_2$-macroglobulin luciferase reporter, 50 ng of c-Jun and increasing amounts of either Stat3 or Stat1 as indicated. (C) Stat1 is functionally active upon IFN-γ treatment in HepG2 cells. Left panel, EMSA with 32P-labeled $\alpha_2$MGAS probe. IL-6 treatment led to the activation of Stat1 and Stat3, while IFN-γ treatment led to the activation of Stat1 in HepG2 cells. SIF A, Stat3 homodimer; SIF B, Stat3:Stat1 heterodimer; SIF C, Stat1 homodimer. Right panel, IFN-γ induced activation of Stat1 with the reporter gene 3xLy6 E, not with $\alpha_2$M, the $\alpha_2$-macroglobulin reporter gene.

Stat3 and c-Jun Cooperatively Activate an IL-6-Inducible $_2$-Macroglobulin Reporter Gene Containing Both Stat and c-Jun Binding Sites The DNA segment from the $_2$-macroglobulin gene (–189 to –95) contains a Stat binding site (a "GAS" element identified by the TTN5AA motif) and an AP-1 binding site and both sites are required for maximal IL-6 induced transcription (18, 20, 30). This DNA segment was therefore used as the enhancer of a luciferase reporter gene construct. HepG2 cells express endogenous Stat3, Stat1 and c-Jun and cells transfected with the reporter gene construct by itself responded with approximately a 7-fold IL-6 induced transcriptional response (FIG. 6A, vector lane). Thus supplemental effects of wild type proteins or interfering effects of mutants must be distinguished from this rather high background. Transfection of the reporter gene and the expression vector for wild-type Stat3 boosted the IL-6 dependent response to about 15-fold. Transfection of the c-Jun vector did not increase the IL-6 induced transcription. Simultaneous transfection of the vectors for wild-type Stat3 and that for c-Jun led to an IL-6 dependent response of the reporter gene of approximately 30-fold (FIG. 6A, lane marked Stat3+ J). These results plus the earlier work from other labs showing binding sites for each type of factor to be required is the basis for concluding there may be a physical interaction between Stat3 and c-Jun in stimulating transcription.

The above results with wild-type Stat3 provided a basis for comparing the function of mutant Stat3 molecules. All three mutants tested (L148A, V151A and TKR) by themselves without extra c-Jun improved the IL-6 dependent response to almost the same extent as did wild-type Stat3 implying the mutations did not affect the protein in some drastic or undefined manner (FIG. 6A, lanes marked with each mutant designation). However, none of the mutants gave appreciable cooperation in the presence of extra c-Jun. These results support the conclusion that the mutations in regions 1 and 2 of Stat3 (FIGS. 4 and 5) block the cooperation between Stat3 and c-Jun.

Figure 6B:
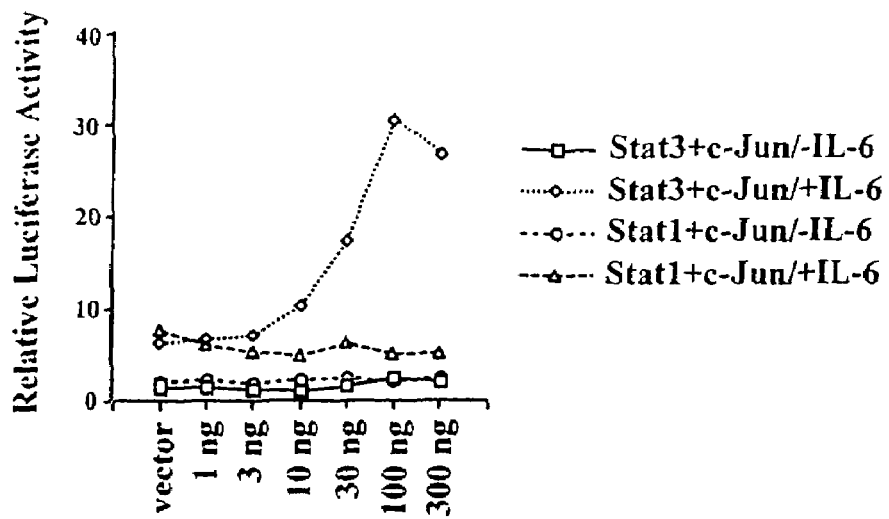
Figure 6C:
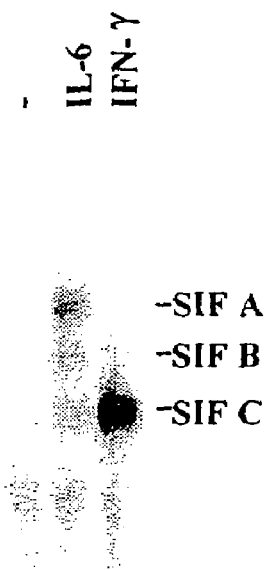
Figure 6D:
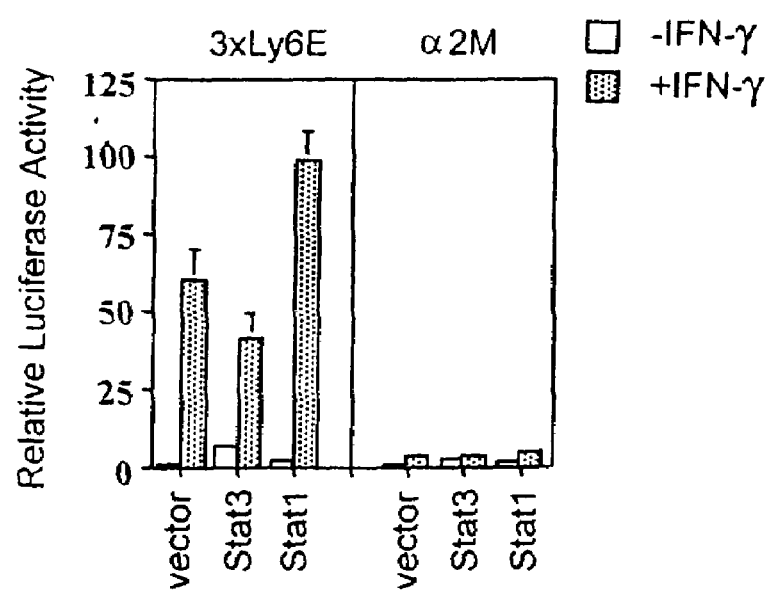

A more thorough examination by transient transfection of the effects of Stat1 on transcription driven by the $\alpha_2$-macroglobulin enhancer was performed. There was no stimulation of transcription of the reporter gene by Stat1 compared to the vector alone (FIG. 6A, Stat1 lane) in contrast to extra added Stat3. Stat1 along with c-Jun also was ineffective in boosting the IL-6 dependent response (FIG. 6A, Stat1+J lane). Even high concentrations of the Stat1 expression vector failed to cooperate with c-Jun to stimulate transcription (FIG. 6B) whereas increasing Stat3 concentration together with extra c-Jun progressively supplemented the IL-6 response to a maximum of about four-fold above background (FIG. 6B). It was observed, however, as has been repeatedly reported, that IL-6 at 5 ng/ml, the concentration used in these experiments, did activate both Stat1 and Stat3 as DNA binding proteins (FIG. 6C, left panel). The same experiment was also performed at 10 ng/ml IL-6 with a consequent stronger induction of Stat1 DNA binding activity. Again however there was no evidence of a supplemental transcriptional stimulation by Stat1 (data not shown).

Whether the $\alpha_2$-macroglobulin promoter would respond to Stat1 if that molecule were stimulated by IFN-γ was then determined. In spite of very strong Stat DNA binding activity, IFN-γ did not activate the $\alpha_2$-macroglobulin enhancer. Moreover whether extra Stat1 or Stat3 was supplied (FIG. 6C, right panel) IFN-γ did not activate transcription driven by the $\alpha_2$-macroglobulin promoter. Functional activation by IFN-γ of endogenous and supplemental Stat1 in HepG2 cells did however activate the known Stat1 or Stat3 sensitive synthetic promoter, Ly6E (FIG. 6C, right panel) that contains three (not a single) Stat binding sites. This reporter gene, long known to respond to IFN-γ (11, 39), was stimulated about 50-fold by endogenous protein (Stat1) and this response was doubled by additional Stat1 expression. So there is no doubt that Stat1 can be activated in HepG2 cells but it does not participate in activating transcription driven by the $\alpha_2$-macroglobulin enhancer.

EXAMPLE 6

Figure 7A:
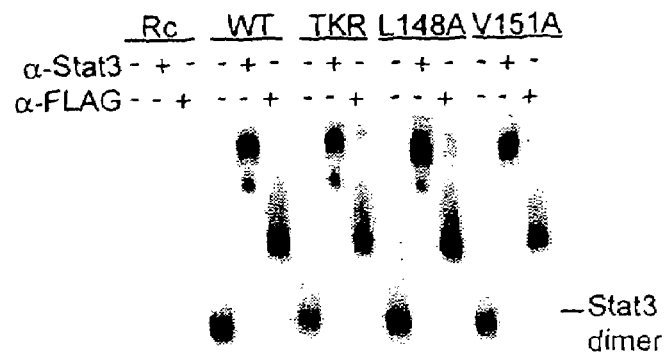
FIG. 7 A–C. The non-interactive Stat3 mutants can bind DNA and activate IL-6 dependent transcription. (A) The DNA binding ability of three non-interactive Stat3 mutants was examined using gel mobility shift analysis with 32P-labeled M67 probe. 293T cells were transiently transfected with either wild-type Stat3 or mutant Stat3 cDNAs, treated with IL-6 at a concentration of 5 ng/ml and recombinant human IL-6 soluble receptor at a concentration of 5 ng/ml for 30 min. Nuclear extracts were prepared from these cells and 3 mg of extract were used in each EMSA. (B) Phosphorylation on tyrosine and serine residues of the three Stat3 mutants was indistinguishable from wild-type Stat3. 75 mg of nuclear extracts from transfected 293T cells were immunoprecipitated with anti-FLAG antibody, and the immunoprecipitates were then subjected to 7% SDS/PAGE, followed by Western blotting with antibodies indicated. Rc, pRcCMV. (C) The IL-6 dependent transcriptional activity of three Stat3 mutants was examined using 3xLy6E luciferase reporter.
Figure 7B:
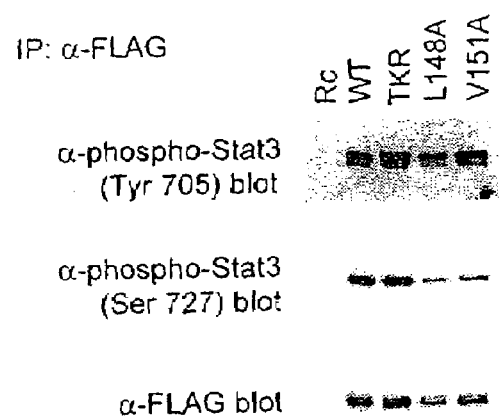
Figure 7C:
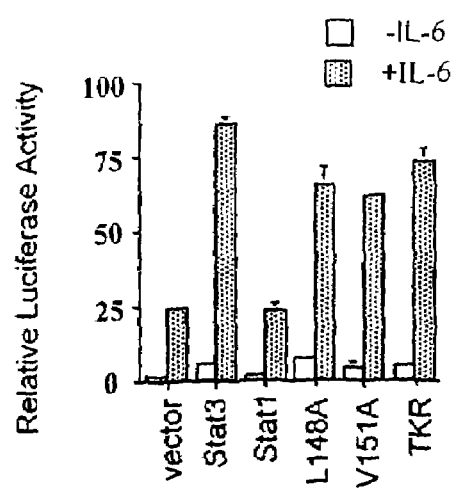

The Non-Interactive Stat3 Mutants can Bind DNA and Activate Non-Cooperative IL-6 Induced Transcription The coil-coil and DNA-binding region mutants fail to cooperate with c-Jun but it was necessary to determine whether these proteins retained the ability on their own to stimulate IL-6 driven transcription. First, the DNA binding ability of the Stat3 mutants compared with that of wild-type protein was examined by overexpression of proteins in 293T cells since these cells are known to have relatively low level of endogenous Stat3 and Stat1 proteins. Cells expressing either wild-type Stat3 or Stat3 mutants were treated with IL-6 and IL-6 soluble receptor for 30 min, and nuclear extracts were prepared. All three of the Stat3 mutants showed DNA-binding ability indistinguishable from wild type Stat3 in a standard EMSA using a $^{32}$P-labeled M67 probe (FIG. 7A). Antibody mediated supershift experiments proved the complexes to be specific. The overexpressed proteins were tagged with the FLAG epitope, and both anti-FLAG and anti-Stat3 antibodies retarded the complexes (Stat1 antibody had no effect on these complexes, data not shown). In addition, both wild-type and mutant proteins were phosphorylated on tyrosine and serine, as tested by Western blot using anti-phospho-Stat3 (Tyr 705) and anti-phospho-Stat3 (Ser 727) antibodies (FIG. 7B). The IL-6 dependent transcriptional activity of three Stat3 mutants was also evaluated in transient transfection assays using the reporter gene containing three copies of Ly6E sites which has been shown to be dependent on Stat3 for IL-6 activated transcription in HepG2 cells (34). All of the proteins were capable of driving transcription of this reporter gene (FIG. 7C), indicating successful activation, dimerization, nuclear translocation, DNA binding, and communication with the basal RNA pol II machinery. For all purposes other than c-Jun binding, these proteins are indistinguishable from wild type protein.

The following citations are referred to above. Each is incorporated herein by reference in its entirety.

1. Alani, R., P. Brown, B. Binetruy, H. Dosaka, R. K. Rosenberg, P. Angel, M. Karin, and M. J. Birrer. 1991. The transactivating domain of the c-Jun proto-oncoprotein is required for cotransformation of rat embryo cells. Mol Cell Biol 11:6286–95.
2. Ausubel, F. M., R. Brent, R. E. Kingston, D. D. Moore, J. G. Seidman, J. A. Smith, and K. Struhl. 1994. Current Protocols in Molecular Biology. John Wiley & Sons, Inc.
3. Baichwal, V. R., and R. Tjian. 1990. Control of c-Jun activity by interaction of a cell-specific inhibitor with regulatory domain delta: differences between v- and c-Jun. Cell 63:815–25.
4. Becker, S., B. Groner, and C. W. Muller. 1998. Three-dimensional structure of the Stat3beta homodimer bound to DNA. Nature 394:145–151.
5. Bohmann, D., and R. Tjian. 1989. Biochemical analysis of transcriptional activation by Jun: differential activity of c- and v-Jun. Cell 59:709–17.
6. Bromberg, J. F., C. M. Horvath, D. Besser, W. W. Lathem, and J. E. Darnell, Jr. 1998. Stat3 activation is required for cellular transformation by v-src. Mol. Cell. Biol. 18:2553–2558.
7. Bromberg, J. F., C. M. Horvath, Z. Wen, R. D. Schreiber, and J. E. Darnell, Jr. 1996. Transcriptionally active Stat1 is required for the antiproliferative effects of both IFN-α and IFN-γ. Proc. Natl. Acad. Sci. USA 93:7673–7678.
8. Carey, M. 1998. The enhanceosome and transcriptional synergy. Cell 92:5–8.
9. Chen, X., U. Vinkemeier, Y. Zhao, D. Jeruzalmi, J. E. Darnell, Jr., and J. Kuriyan. 1998. Crystal structure of a tyrosine phosphorylated Stat-1 dimer bound to DNA. Cell 93:827–839.
10. Chin, Y. E., M. Kitagawa, W. C. Su, Z. H. You, Y. Iwamoto, and X. Y. Fu. 1996. Cell growth arrest and induction of cyclin-dependent kinase inhibitor p21 WAF1/CIP1 mediated by Stat1. Science 272:719–22.
11. Darnell, J. E., Jr. 1997. Stats and gene regulation. Science 277:1630–1635.
12. Fann, M. J., and P. H. Patterson. 1993. A novel approach to screen for cytokine effects on neuronal gene expression. J. Neurochem. 61:1349–1355.
13. Fried, M., and D. M. Crothers. 1981. Equilibria and kinetics of lac repressor-operator interactions by polyacrylamide gel electrophoresis. Nucl. Acids Res. 9:6505–6525.
14. Garcia, R., C. L. Yu, A. Hudnall, R. Catlett, K. L. Nelson, T. Smithgall, D. J. Fujita, S. P. Ethier, and R. Jove. 1997. Constitutive activation of Stat3 in fibroblasts transformed by diverse oncoproteins and in breast carcinoma cells. Cell Growth Differ 8:1267–76.
15. Giese, K., C. Kingsley, J. R. Kirshner, and R. Grosschedl. 1995. Assembly and function of a TCR α enhancer complex is dependent on LEF-1-induced DNA bending and multiple protein-protein interactions. Genes Dev 9:995–1008.
16. Glover, J. N. M., and S. C. Harrison. 1995. Crystal structure of the heterodimeric bZIP transcription factor c-Fos-c-Jun bound to DNA. Nature 373:257–261.
17. Guyer, N. B., C. W. Severns, P. Wong, C. A. Feghali, and T. M. Wright. 1995. IFN-γ induces a p91/Stat1a-related transcription factor with distinct activation and binding properties. J. Immunol. 155:3472–3480.
18. Heinrich, P. C., F. Horn, L. Graeve, E. Dittrich, I. Kerr, G. Muller-Newen, J. Grotzinger, and A. Wollmer. 1998. Interleukin-6 and related cytokines: effect on the acute phase reaction. Z Ernahrungswiss 37:43–9.
19. Horvath, C. M., G. R. Stark, I. M. Kerr, and J. E. Darnell, Jr. 1996. Interactions between Stat and non-Stat proteins in the ISGF3 complex. Mol. Cell. Biol. 16:6957–6964.
20. Ito, T., H. Tanahashi, Y. Misumi, and Y. Sakaki. 1989. Nuclear factors interacting with an interleukin-6 responsive element of rat alpha 2-macroglobulin gene. Nucleic Acids Res 17:9425–35.
21. Kim, T. K., and T. Maniatis. 1997. The mechanism of transcriptional synergy of an in vitro assembled interferon-beta enhanceosome. Mol Cell 1:119–29.
22. Korzus, E., H. Nagase, R. Rydell, and J. Travis. 1997. The mitogen-activated protein kinase and JAK-Stat signaling pathways are required for an oncoStatin M-responsive element-mediated activation of matrix metalloproteinase 1 gene expression. J Biol Chem 272:1188–96.
23. Lewis, S. E., M. S. Rao, A. J. Symes, W. T. Dauer, J. S. Fink, S. C. Landis, and S. E. Hyman. 1994. Coordinate regulation of choline acetyltransferase, tyrosine hydroxylase, and neuropeptide mRNAs by ciliary neurotrophic factor and leukemia inhibitory factor in cultured sympathetic neurons. J. Neurochem. 63:429–438.
24. Look, D. C., M. R. Pelletier, and M. J. Holtzman. 1994. Selective interaction of a subset of interferon-gamma response element-binding proteins with the intercellular adhesion molecule-1 (ICAM-1) gene promoter controls the pattern of expression on epithelial cells. J. Biol. Chem. 269:8952–8958.

25. Mayall, T. P., P. L. Sheridan, M. R. Montniiny, and K. A. Jones. 1997. Distinct roles for P-CREB and LEF-1 in TCR alpha enhancer assembly and activation on chromatin templates in vitro. Genes Dev 11:887–99.
26. Mirkovitch, J., T. Decker, and J. E. Darnell, Jr. 1992. Interferon induction of gene transcription analyzed by in vivo footprinting. Mol Cell Biol 12:1–9.
27. Robertson, L. M., T. K. Kerppola, M. Vendrell, D. Luk, R. J. Smeyne, C. Bocchiaro, J. I. Morgan, and T. Curran. 1995. Regulation of c-fos expression in transgenic mice requires multiple interdependent transcription control elements. Neuron 14:241–52.
28. Roeder, R. G. 1997. The role of general initiation factors in transcription by RNA polymerase II. Trends Biochem. Sci. 21:327–335.
29. Sadowski, H. B., K. Shuai, J. E. Darnell, Jr., and M. Z. Gilman. 1993. A common nuclear signal transduction pathway activated by growth factor and cytokine receptors. Science 261:1739–1744.
30. Schaefer, T. S., L. K. Sanders, and D. Nathans. 1995. Cooperative transcriptional activity of Jun and Stat3b, a short form of Stat3. Proc. Natl. Acad. Sci. USA 92:9097–9101.
31. Schaefer, T. S., L. K. Sanders, 0. K. Park, and D. Nathans. 1997. Functional differences between Stat3a and Stat3b. Mol. Cell. Biol. 17:5307–5316.
32. Schindler, C., X.-Y. Fu, T. Improta, R. Aebersold, and J. E. Darnell, Jr. 1992. Proteins of transcription factor ISGF-3: One gene encodes the 91 and 84 kDA ISGF-3 proteins that are activated by interferon-. Proc. Natl. Acad. Sci. USA 89:7836–7839.
33. Schindler, C., K. Shuai, V. R. Prezioso, and J. E. Darnell, Jr. 1992. Interferon-dependent tyrosine phosphorylation of a latent cytoplasmic transcription factor. Science 257: 809–815.
34. Sengupta, T. K., E. S. Talbot, P. A. Scherle, and L. Ivashkiv. 1998. Rapid inhibition of interleukin-6 signaling and Stat3 activation mediated by mitogen-activated protein kinases. Proc. Natl. Acad. Sci. USA 95:11107–11112.
35. Shuai, K., C. Schindler, V. R. Prezioso, and J. E. Darnell, Jr. 1992. Activation of transcription by IFN-γ: tyrosine phosphorylation of a 91 kD DNA binding protein. Science 259:1808–1812.
36. Symes, A., S. Lewis, L. Corpus, P. Rajan, S. E. Human, and J. S. Fink. 1994. Stat proteins participate in the regulation of the vasoactive intestinal peptide gene by the ciliary neurotrophic factor family of cytokines. Mol. Endocrin. 8:1750–1763.
37. Thanos, D., and T. Maniatis. 1995. Virus induction of human IFNβ gene expression requires the assembly of an enhanceosome. Cell 83:1091–1100.
38. Wagner, B. J., T. E. Hayes, C. J. Hoban, and B. H. Cochran. 1990. The SIF binding element confers sis/PDGF inducibility onto the c-fos promoter. EMBO J. 9:4477–4484.
39. Wen, Z., Z. Zhong, and J. E. Darnell, Jr. 1995. Maximal activation of transcription of Stat1 and Stat3 requires both tyrosine and serine phosphorylation. Cell 82:241–250.
40. Werb, Z., C. M. Alexander, and R. R. Adler. 1992. In Matrix Metalloproteinases and Inhibitors (Birkedal-Hansen, H., Werb, Z., Velgus, H. G., and Van Wart, H. E., eds) pp. 337–343, Gustav Fisher, Stuttgart.
41. Xu, X. A., Y. L. Sun, and T. Hoey. 1996. Cooperative DNA binding and sequence selective recognition conferred by the Stat amino terminal domain. Science 273: 794–797.
42. Yu, C. L., D. J. Meyer, G. S. Campbell, A. C. Larner, C. Carter-Su, J. Schwartz, and R. Jove. 1995. Enhanced DNA-binding activity of a Stat3-related protein in cells transformed by the Src oncoprotein. Science 269:81–3.
43. Zhang, J. J., U. Vinkemeier, W. Gu, D. Chakravarti, C. M. Horvath, and J. E. Darnell, Jr. 1996. Two contact regions between Stat1 and CBP/p300 in interferon γ signaling. Proc. Natl. Acad. Sci. USA 93:15092–15096.
44. Zhong, Z., Z. Wen, and J. E. Darnell, Jr. 1994. Stat3 and Stat4: Members of the family of signal transducers and activators of transcription. Proc. Natl. Acad. Sci. USA 91:4806–4810.
45. Zhong, Z., Z. Wen, and J. E. Darnell, Jr. 1994. Stat3: A Stat family member activated by tyrosine phosphorylation in response to epidermal growth factor and interleukin-6. Science 264:95–98.

What is claimed is:

1. A polynucleotide encoding a Stat fragment selected from the group consisting of residues 1–154 of Stat3 (SEQ ID NO:8), residues 107–377 of Stat3 (SEQ ID NO:9), residues 107–358 of Stat3 (SEQ ID NO:14), residues 107–342 of Stat3 (SEQ ID NO:15), residues 107–282 of Stat3 (SEQ ID NO:16), residues 107–249 of Stat3 (SEQ ID NO:17), residues 130–358 of Stat3 (SEQ ID NO:18), residues 130–342 of Stat3 (SEQ ID NO:19), residues 155–282 of Stat3 (SEQ ID NO:20), residues 155–249 of Stat3 (SEQ ID NO:21), residues 155–377 of Stat3 (SEQ ID NO:22), residues 193–377 of Stat3 (SEQ ID NO:23); residues 249–377 of Stat3 (SEQ ID NO:24); and residues 282–377 of Stat3 (SEQ ID NO:25).

2. A polynucleotide encoding a Stat3 mutant consisting of Stat3(L148A) (SEQ ID NO:30), Stat3(V151A) (SEQ ID NO:31), or Stat3(T346A, K348A, R350A) (SEQ ID NO:29).

3. A cell transiently expressing a mutant Stat3 protein consisting of Stat3(L148A) (SEQ ID NO:30), Stat3(V151A) (SEQ ID NO:31), or Stat3(T346A, K348A, R350A) (SEQ ID NO:29).

* * * * *

SEQUENCE LISTING

<160> NUMBER OF SEQ ID NOS: 43

<210> SEQ ID NO 1
<211> LENGTH: 39
<212> TYPE: DNA
<213> ORGANISM: Mus musculus
<220> FEATURE:
<223> OTHER INFORMATION: Description of Artificial Sequence: Primer

<400> SEQUENCE: 1
cacccaacag ccgccgtagc aacagagaag cagvagatg                                  39

<210> SEQ ID NO 2
<211> LENGTH: 39
<212> TYPE: DNA
<213> ORGANISM: Mus musculus
<220> FEATURE:
<223> OTHER INFORMATION: Description of Artificial Sequence: Primer

```
<400> SEQUENCE: 2
gccgtagtga cagagaaggc acagatgttg gagcagcat                                      39

<210> SEQ ID NO 3
<211> LENGTH: 51
<212> TYPE: DNA
<213> ORGANISM: Mus musculus
<220> FEATURE:
<223> OTHER INFORMATION: Description of Artificial Sequence: Primer

<400> SEQUENCE: 3
gccgtagtga cagagaagca gcagatggca gagcagcatc ttcaggatgt c                        51

<210> SEQ ID NO 4
<211> LENGTH: 34
<212> TYPE: DNA
<213> ORGANISM: Mus musculus
<220> FEATURE:
<223> OTHER INFORMATION: Description of Artificial Sequence: Primer

<400> SEQUENCE: 4
atgttggagc agcatgctca ggatgtccgg aagc                                           34

<210> SEQ ID NO 5
<211> LENGTH: 35
<212> TYPE: DNA
<213> ORGANISM: Mus musculus
<220> FEATURE:
<223> OTHER INFORMATION: Description of Artificial Sequence: Primer

<400> SEQUENCE: 5
gcagcatctt caggatgcac ggaagcgagt gcagg                                          35

<210> SEQ ID NO 6
<211> LENGTH: 58
<212> TYPE: DNA
<213> ORGANISM: Mus musculus
<220> FEATURE:
<223> OTHER INFORMATION: Description of Artificial Sequence: Primer

<400> SEQUENCE: 6
caactcagga aatttgacca gcaacgcgac tgccgtggca aactggacac cagtcttg                 58

<210> SEQ ID NO 7
<211> LENGTH: 17
<212> TYPE: DNA
<213> ORGANISM: Mus musculus
<220> FEATURE:
<223> OTHER INFORMATION: Description of Artificial Sequence: Primer

<400> SEQUENCE: 7
aatccttctg ggaattc                                                              17

<210> SEQ ID NO 8
<211> LENGTH: 154
<212> TYPE: PRT
<213> ORGANISM: Mus musculus

<400> SEQUENCE: 8

Met Ala Gln Trp Asn Gln Leu Gln Gln Leu Asp Thr Arg Tyr Leu Lys
  1               5                  10                  15

Gln Leu His Gln Leu Tyr Ser Asp Thr Phe Pro Met Glu Leu Arg Gln
             20                  25                  30
```

```
Phe Leu Ala Pro Trp Ile Glu Ser Gln Asp Trp Ala Tyr Ala Ala Ser
         35                  40                  45

Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
130                 135                 140

Glu Gln His Leu Gln Asp Val Arg Lys Arg
145                 150
```

<210> SEQ ID NO 9
<211> LENGTH: 271
<212> TYPE: PRT
<213> ORGANISM: Mus musculus

<400> SEQUENCE: 9

```
Arg Cys Leu Trp Glu Glu Ser Arg Leu Leu Gln Thr Ala Ala Thr Ala
  1               5                  10                  15

Ala Gln Gln Gly Gly Gln Ala Asn His Pro Thr Ala Ala Val Val Thr
             20                  25                  30

Glu Lys Gln Gln Met Leu Glu Gln His Leu Gln Asp Val Arg Lys Arg
         35                  40                  45

Val Gln Asp Leu Glu Gln Lys Met Lys Val Val Glu Asn Leu Gln Asp
 50                  55                  60

Asp Phe Asp Phe Asn Tyr Lys Thr Leu Lys Ser Gln Gly Asp Met Gln
 65                  70                  75                  80

Asp Leu Asn Gly Asn Asn Gln Ser Val Thr Arg Gln Lys Met Gln Gln
                 85                  90                  95

Leu Glu Gln Met Leu Thr Ala Leu Asp Gln Met Arg Arg Ser Ile Val
                100                 105                 110

Ser Glu Leu Ala Gly Leu Leu Ser Ala Met Glu Tyr Val Gln Lys Thr
            115                 120                 125

Leu Thr Asp Glu Glu Leu Ala Asp Trp Lys Arg Arg Pro Glu Ile Ala
130                 135                 140

Cys Ile Gly Gly Pro Pro Asn Ile Cys Leu Asp Arg Leu Glu Asn Trp
145                 150                 155                 160

Ile Thr Ser Leu Ala Glu Ser Gln Leu Gln Thr Arg Gln Gln Ile Lys
                165                 170                 175

Lys Leu Glu Glu Leu Gln Gln Lys Val Ser Tyr Lys Gly Asp Pro Ile
                180                 185                 190

Val Gln His Arg Pro Met Leu Glu Glu Arg Ile Val Glu Leu Phe Arg
            195                 200                 205

Asn Leu Met Lys Ser Ala Phe Val Val Glu Arg Gln Pro Cys Met Pro
210                 215                 220

Met His Pro Asp Arg Pro Leu Val Ile Lys Thr Gly Val Gln Phe Thr
225                 230                 235                 240

Thr Lys Val Arg Leu Leu Val Lys Phe Pro Glu Leu Asn Tyr Gln Leu
                245                 250                 255
```

```
Lys Ile Lys Val Cys Ile Asp Lys Asp Ser Gly Asp Val Ala Ala
            260                 265                 270
```

<210> SEQ ID NO 10
<211> LENGTH: 393
<212> TYPE: PRT
<213> ORGANISM: Mus musculus

<400> SEQUENCE: 10

```
Leu Arg Gly Ser Arg Lys Phe Asn Ile Leu Gly Thr Asn Thr Lys Val
  1               5                  10                  15

Met Asn Met Glu Glu Ser Asn Asn Gly Ser Leu Ser Ala Glu Phe Lys
             20                  25                  30

His Leu Thr Leu Arg Glu Gln Arg Cys Gly Asn Gly Gly Arg Ala Asn
         35                  40                  45

Cys Asp Ala Ser Leu Ile Val Thr Glu Glu Leu His Leu Ile Thr Phe
 50                  55                  60

Glu Thr Glu Val Tyr His Gln Gly Leu Lys Ile Asp Leu Glu Thr His
 65                  70                  75                  80

Ser Leu Pro Val Val Ile Ser Asn Ile Cys Gln Met Pro Asn Ala
                 85                  90                  95

Trp Ala Ser Ile Leu Trp Tyr Asn Met Leu Thr Asn Pro Lys Asn
                100                 105                 110

Val Asn Phe Phe Thr Lys Pro Pro Ile Gly Thr Trp Asp Gln Val Ala
            115                 120                 125

Glu Val Leu Ser Trp Gln Phe Ser Ser Thr Thr Lys Arg Gly Leu Ser
        130                 135                 140

Ile Glu Gln Leu Thr Thr Leu Ala Glu Lys Leu Leu Gly Pro Gly Val
145                 150                 155                 160

Asn Tyr Ser Gly Cys Gln Ile Thr Trp Ala Lys Phe Cys Lys Glu Asn
                165                 170                 175

Met Ala Gly Lys Gly Phe Ser Phe Trp Val Trp Leu Asp Asn Ile Ile
            180                 185                 190

Asp Leu Val Lys Lys Tyr Ile Leu Ala Leu Trp Asn Glu Gly Tyr Ile
        195                 200                 205

Met Gly Phe Ile Ser Lys Glu Arg Glu Arg Ala Ile Leu Ser Thr Lys
    210                 215                 220

Pro Pro Gly Thr Phe Leu Leu Arg Phe Ser Glu Ser Ser Lys Glu Gly
225                 230                 235                 240

Gly Val Thr Phe Thr Trp Val Glu Lys Asp Ile Ser Gly Lys Thr Gln
                245                 250                 255

Ile Gln Ser Val Glu Pro Tyr Thr Lys Gln Gln Leu Asn Asn Met Ser
            260                 265                 270

Phe Ala Glu Ile Ile Met Gly Tyr Lys Ile Met Asp Ala Thr Asn Ile
        275                 280                 285

Leu Val Ser Pro Leu Val Tyr Leu Tyr Pro Asp Ile Pro Lys Glu Glu
    290                 295                 300

Ala Phe Gly Lys Tyr Cys Arg Pro Glu Ser Gln Glu His Pro Glu Ala
305                 310                 315                 320

Asp Pro Gly Ser Ala Ala Pro Tyr Leu Lys Thr Lys Phe Ile Cys Val
                325                 330                 335

Thr Pro Thr Thr Cys Ser Asn Thr Ile Asp Leu Pro Met Ser Pro Arg
            340                 345                 350

Thr Leu Asp Ser Leu Met Gln Phe Gly Asn Asn Gly Glu Gly Ala Glu
```

```
                355                 360                 365
Pro Ser Ala Gly Gly Gln Phe Glu Ser Leu Thr Phe Asp Met Asp Leu
        370                 375                 380

Thr Ser Glu Cys Ala Thr Ser Pro Met
385                 390

<210> SEQ ID NO 11
<211> LENGTH: 154
<212> TYPE: PRT
<213> ORGANISM: Mus musculus

<400> SEQUENCE: 11

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met
145                 150

<210> SEQ ID NO 12
<211> LENGTH: 268
<212> TYPE: PRT
<213> ORGANISM: Mus musculus

<400> SEQUENCE: 12

Ser Cys Leu Lys Glu Glu Arg Lys Ile Leu Glu Asn Ala Gln Arg Phe
1               5                   10                  15

Asn Gln Ala Gln Ser Gly Asn Ile Gln Ser Thr Val Met Leu Asp Lys
            20                  25                  30

Gln Lys Glu Leu Asp Ser Lys Val Arg Asn Val Lys Asp Lys Val Met
        35                  40                  45

Cys Ile Glu His Glu Ile Lys Ser Leu Glu Asp Leu Gln Asp Glu Tyr
    50                  55                  60

Asp Phe Lys Cys Lys Thr Leu Gln Asn Arg Glu His Glu Thr Asn Gly
65                  70                  75                  80

Val Ala Lys Ser Asp Gln Lys Gln Glu Gln Leu Leu Leu Lys Lys Met
                85                  90                  95

Tyr Leu Met Leu Asp Asn Lys Arg Lys Glu Val Val His Lys Ile Ile
            100                 105                 110

Glu Leu Leu Asn Val Thr Glu Leu Thr Gln Asn Ala Leu Ile Asn Asp
        115                 120                 125

Glu Leu Val Glu Trp Lys Arg Arg Gln Gln Ser Ala Cys Ile Gly Gly
```

```
                130                 135                 140
Pro Pro Asn Ala Cys Leu Asp Gln Leu Gln Asn Trp Phe Thr Ile Val
145                 150                 155                 160

Ala Glu Ser Leu Gln Gln Val Arg Gln Gln Leu Lys Lys Leu Glu Glu
                165                 170                 175

Leu Glu Gln Lys Tyr Thr Tyr Glu His Asp Pro Ile Thr Lys Asn Lys
            180                 185                 190

Gln Val Leu Trp Asp Arg Thr Phe Ser Leu Phe Gln Gln Leu Ile Gln
        195                 200                 205

Ser Ser Phe Val Val Glu Arg Gln Pro Cys Met Pro Thr His Pro Gln
210                 215                 220

Arg Pro Leu Val Leu Lys Thr Gly Val Gln Phe Thr Val Lys Leu Arg
225                 230                 235                 240

Leu Leu Val Lys Leu Gln Glu Leu Asn Tyr Asn Leu Lys Val Lys Val
                245                 250                 255

Leu Phe Asp Lys Asp Val Asn Glu Arg Asn Thr Val
            260                 265
```

<210> SEQ ID NO 13
<211> LENGTH: 376
<212> TYPE: PRT
<213> ORGANISM: Mus musculus

<400> SEQUENCE: 13

```
Lys Gly Phe Arg Lys Phe Asn Ile Leu Gly Thr His Thr Lys Val Met
  1               5                  10                  15

Asn Met Glu Glu Ser Thr Asn Gly Ser Leu Ala Ala Glu Phe Arg His
                20                  25                  30

Leu Gln Leu Lys Glu Gln Lys Asn Ala Gly Thr Arg Thr Asn Glu Gly
            35                  40                  45

Pro Leu Ile Val Thr Glu Glu Leu His Ser Leu Ser Phe Glu Thr Gln
        50                  55                  60

Leu Cys Gln Pro Gly Leu Val Ile Asp Leu Glu Thr Thr Ser Leu Pro
 65                  70                  75                  80

Val Val Val Ile Ser Asn Val Ser Gln Leu Pro Ser Gly Trp Ala Ser
                 85                  90                  95

Ile Leu Trp Tyr Asn Met Leu Val Ala Glu Pro Arg Asn Leu Ser Phe
                100                 105                 110

Phe Leu Thr Pro Pro Cys Ala Arg Trp Ala Gln Leu Ser Glu Val Leu
            115                 120                 125

Ser Trp Gln Phe Ser Ser Val Thr Lys Arg Gly Leu Asn Val Asp Gln
        130                 135                 140

Leu Asn Met Leu Gly Glu Lys Leu Leu Gly Pro Asn Ala Ser Pro Asp
145                 150                 155                 160

Gly Leu Ile Pro Trp Thr Arg Phe Cys Lys Glu Asn Ile Asn Asp Lys
                165                 170                 175

Asn Phe Pro Phe Trp Leu Trp Ile Glu Ser Ile Leu Glu Leu Ile Lys
            180                 185                 190

Lys His Leu Leu Pro Leu Trp Asn Asp Gly Cys Ile Met Gly Phe Ile
        195                 200                 205

Ser Lys Glu Arg Glu Arg Ala Leu Leu Lys Asp Gln Gln Pro Gly Thr
210                 215                 220

Phe Leu Leu Arg Phe Ser Glu Ser Ser Arg Glu Gly Ala Ile Thr Phe
225                 230                 235                 240
```

```
Thr Trp Val Glu Arg Ser Gln Asn Gly Gly Glu Pro Asp Phe His Ala
            245                 250                 255

Val Glu Pro Tyr Thr Lys Lys Glu Leu Ser Ala Val Thr Phe Pro Asp
                260                 265                 270

Ile Ile Arg Asn Tyr Lys Val Met Ala Ala Glu Asn Ile Pro Glu Asn
            275                 280                 285

Pro Leu Lys Tyr Leu Tyr Pro Asn Ile Asp Lys Asp His Ala Phe Gly
        290                 295                 300

Lys Tyr Tyr Ser Arg Pro Lys Glu Ala Pro Glu Pro Met Glu Leu Asp
305                 310                 315                 320

Gly Pro Lys Gly Thr Gly Tyr Ile Lys Thr Glu Leu Ile Ser Val Ser
                325                 330                 335

Glu Val His Pro Ser Arg Leu Gln Thr Thr Asp Asn Leu Leu Pro Met
                340                 345                 350

Ser Pro Glu Glu Phe Asp Glu Val Ser Arg Ile Val Gly Ser Val Glu
                355                 360                 365

Phe Asp Ser Met Met Asn Thr Val
        370                 375

<210> SEQ ID NO 14
<211> LENGTH: 252
<212> TYPE: PRT
<213> ORGANISM: Mus musculus

<400> SEQUENCE: 14

Arg Cys Leu Trp Glu Glu Ser Arg Leu Leu Gln Thr Ala Ala Thr Ala
  1               5                  10                  15

Ala Gln Gln Gly Gly Gln Ala Asn His Pro Thr Ala Ala Val Val Thr
                20                  25                  30

Glu Lys Gln Gln Met Leu Glu Gln His Leu Gln Asp Val Arg Lys Arg
            35                  40                  45

Val Gln Asp Leu Glu Gln Lys Met Lys Val Val Glu Asn Leu Gln Asp
        50                  55                  60

Asp Phe Asp Phe Asn Tyr Lys Thr Leu Lys Ser Gln Gly Asp Met Gln
 65                  70                  75                  80

Asp Leu Asn Gly Asn Asn Gln Ser Val Thr Arg Gln Lys Met Gln Gln
                85                  90                  95

Leu Glu Gln Met Leu Thr Ala Leu Asp Gln Met Arg Arg Ser Ile Val
            100                 105                 110

Ser Glu Leu Ala Gly Leu Leu Ser Ala Met Glu Tyr Val Gln Lys Thr
        115                 120                 125

Leu Thr Asp Glu Glu Leu Ala Asp Trp Lys Arg Arg Pro Glu Ile Ala
130                 135                 140

Cys Ile Gly Gly Pro Pro Asn Ile Cys Leu Asp Arg Leu Glu Asn Trp
145                 150                 155                 160

Ile Thr Ser Leu Ala Glu Ser Gln Leu Gln Thr Arg Gln Gln Ile Lys
                165                 170                 175

Lys Leu Glu Glu Leu Gln Gln Lys Val Ser Tyr Lys Gly Asp Pro Ile
            180                 185                 190

Val Gln His Arg Pro Met Leu Glu Glu Arg Ile Val Glu Leu Phe Arg
        195                 200                 205

Asn Leu Met Lys Ser Ala Phe Val Val Glu Arg Gln Pro Cys Met Pro
210                 215                 220

Met His Pro Asp Arg Pro Leu Val Ile Lys Thr Gly Val Gln Phe Thr
225                 230                 235                 240
```

```
Thr Lys Val Arg Leu Leu Val Lys Phe Pro Glu Leu
            245                 250
```

<210> SEQ ID NO 15
<211> LENGTH: 236
<212> TYPE: PRT
<213> ORGANISM: Mus musculus

<400> SEQUENCE: 15

```
Arg Cys Leu Trp Glu Glu Ser Arg Leu Leu Gln Thr Ala Ala Thr Ala
  1               5                  10                  15

Ala Gln Gln Gly Gly Gln Ala Asn His Pro Thr Ala Ala Val Val Thr
             20                  25                  30

Glu Lys Gln Gln Met Leu Glu Gln His Leu Gln Asp Val Arg Lys Arg
         35                  40                  45

Val Gln Asp Leu Glu Gln Lys Met Lys Val Val Glu Asn Leu Gln Asp
     50                  55                  60

Asp Phe Asp Phe Asn Tyr Lys Thr Leu Lys Ser Gln Gly Asp Met Gln
 65                  70                  75                  80

Asp Leu Asn Gly Asn Asn Gln Ser Val Thr Arg Gln Lys Met Gln Gln
                 85                  90                  95

Leu Glu Gln Met Leu Thr Ala Leu Asp Gln Met Arg Arg Ser Ile Val
            100                 105                 110

Ser Glu Leu Ala Gly Leu Leu Ser Ala Met Glu Tyr Val Gln Lys Thr
        115                 120                 125

Leu Thr Asp Glu Glu Leu Ala Asp Trp Lys Arg Arg Pro Glu Ile Ala
    130                 135                 140

Cys Ile Gly Gly Pro Pro Asn Ile Cys Leu Asp Arg Leu Glu Asn Trp
145                 150                 155                 160

Ile Thr Ser Leu Ala Glu Ser Gln Leu Gln Thr Arg Gln Gln Ile Lys
                165                 170                 175

Lys Leu Glu Glu Leu Gln Gln Lys Val Ser Tyr Lys Gly Asp Pro Ile
            180                 185                 190

Val Gln His Arg Pro Met Leu Glu Glu Arg Ile Val Glu Leu Phe Arg
        195                 200                 205

Asn Leu Met Lys Ser Ala Phe Val Val Glu Arg Gln Pro Cys Met Pro
    210                 215                 220

Met His Pro Asp Arg Pro Leu Val Ile Lys Thr Gly
225                 230                 235
```

<210> SEQ ID NO 16
<211> LENGTH: 176
<212> TYPE: PRT
<213> ORGANISM: Mus musculus

<400> SEQUENCE: 16

```
Arg Cys Leu Trp Glu Glu Ser Arg Leu Leu Gln Thr Ala Ala Thr Ala
  1               5                  10                  15

Ala Gln Gln Gly Gly Gln Ala Asn His Pro Thr Ala Ala Val Val Thr
             20                  25                  30

Glu Lys Gln Gln Met Leu Glu Gln His Leu Gln Asp Val Arg Lys Arg
         35                  40                  45

Val Gln Asp Leu Glu Gln Lys Met Lys Val Val Glu Asn Leu Gln Asp
     50                  55                  60

Asp Phe Asp Phe Asn Tyr Lys Thr Leu Lys Ser Gln Gly Asp Met Gln
 65                  70                  75                  80
```

```
Asp Leu Asn Gly Asn Asn Gln Ser Val Thr Arg Gln Lys Met Gln Gln
                    85                  90                  95

Leu Glu Gln Met Leu Thr Ala Leu Asp Gln Met Arg Arg Ser Ile Val
                100                 105                 110

Ser Glu Leu Ala Gly Leu Leu Ser Ala Met Glu Tyr Val Gln Lys Thr
            115                 120                 125

Leu Thr Asp Glu Glu Leu Ala Asp Trp Lys Arg Arg Pro Glu Ile Ala
        130                 135                 140

Cys Ile Gly Gly Pro Pro Asn Ile Cys Leu Asp Arg Leu Glu Asn Trp
145                 150                 155                 160

Ile Thr Ser Leu Ala Glu Ser Gln Leu Gln Thr Arg Gln Gln Ile Lys
                165                 170                 175

<210> SEQ ID NO 17
<211> LENGTH: 143
<212> TYPE: PRT
<213> ORGANISM: Mus musculus

<400> SEQUENCE: 17

Arg Cys Leu Trp Glu Glu Ser Arg Leu Leu Gln Thr Ala Ala Thr Ala
1               5                   10                  15

Ala Gln Gln Gly Gly Gln Ala Asn His Pro Thr Ala Ala Val Val Thr
                20                  25                  30

Glu Lys Gln Gln Met Leu Glu Gln His Leu Gln Asp Val Arg Lys Arg
            35                  40                  45

Val Gln Asp Leu Glu Gln Lys Met Lys Val Val Glu Asn Leu Gln Asp
        50                  55                  60

Asp Phe Asp Phe Asn Tyr Lys Thr Leu Lys Ser Gln Gly Asp Met Gln
65                  70                  75                  80

Asp Leu Asn Gly Asn Asn Gln Ser Val Thr Arg Gln Lys Met Gln Gln
                85                  90                  95

Leu Glu Gln Met Leu Thr Ala Leu Asp Gln Met Arg Arg Ser Ile Val
                100                 105                 110

Ser Glu Leu Ala Gly Leu Leu Ser Ala Met Glu Tyr Val Gln Lys Thr
            115                 120                 125

Leu Thr Asp Glu Glu Leu Ala Asp Trp Lys Arg Arg Pro Glu Ile
        130                 135                 140

<210> SEQ ID NO 18
<211> LENGTH: 229
<212> TYPE: PRT
<213> ORGANISM: Mus musculus

<400> SEQUENCE: 18

Asn His Pro Thr Ala Ala Val Val Thr Glu Lys Gln Gln Met Leu Glu
1               5                   10                  15

Gln His Leu Gln Asp Val Arg Lys Arg Val Gln Asp Leu Glu Gln Lys
                20                  25                  30

Met Lys Val Val Glu Asn Leu Gln Asp Asp Phe Asp Phe Asn Tyr Lys
            35                  40                  45

Thr Leu Lys Ser Gln Gly Asp Met Gln Asp Leu Asn Gly Asn Asn Gln
        50                  55                  60

Ser Val Thr Arg Gln Lys Met Gln Gln Leu Glu Gln Met Leu Thr Ala
65                  70                  75                  80

Leu Asp Gln Met Arg Arg Ser Ile Val Ser Glu Leu Ala Gly Leu Leu
                85                  90                  95
```

```
Ser Ala Met Glu Tyr Val Gln Lys Thr Leu Thr Asp Glu Glu Leu Ala
            100                 105                 110

Asp Trp Lys Arg Arg Pro Glu Ile Ala Cys Ile Gly Gly Pro Pro Asn
            115                 120                 125

Ile Cys Leu Asp Arg Leu Glu Asn Trp Ile Thr Ser Leu Ala Glu Ser
            130                 135                 140

Gln Leu Gln Thr Arg Gln Ile Lys Lys Leu Glu Glu Leu Gln Gln
145                 150                 155                 160

Lys Val Ser Tyr Lys Gly Asp Pro Ile Val Gln His Arg Pro Met Leu
                165                 170                 175

Glu Glu Arg Ile Val Glu Leu Phe Arg Asn Leu Met Lys Ser Ala Phe
            180                 185                 190

Val Val Glu Arg Gln Pro Cys Met Pro Met His Pro Asp Arg Pro Leu
            195                 200                 205

Val Ile Lys Thr Gly Val Gln Phe Thr Thr Lys Val Arg Leu Leu Val
            210                 215                 220

Lys Phe Pro Glu Leu
225

<210> SEQ ID NO 19
<211> LENGTH: 213
<212> TYPE: PRT
<213> ORGANISM: Mus musculus

<400> SEQUENCE: 19

Asn His Pro Thr Ala Ala Val Val Thr Glu Lys Gln Gln Met Leu Glu
  1               5                  10                  15

Gln His Leu Gln Asp Val Arg Lys Arg Val Gln Asp Leu Glu Gln Lys
            20                  25                  30

Met Lys Val Val Glu Asn Leu Gln Asp Asp Phe Asp Phe Asn Tyr Lys
            35                  40                  45

Thr Leu Lys Ser Gln Gly Asp Met Gln Asp Leu Asn Gly Asn Asn Gln
 50                  55                  60

Ser Val Thr Arg Gln Lys Met Gln Gln Leu Glu Gln Met Leu Thr Ala
 65                  70                  75                  80

Leu Asp Gln Met Arg Arg Ser Ile Val Ser Glu Leu Ala Gly Leu Leu
                85                  90                  95

Ser Ala Met Glu Tyr Val Gln Lys Thr Leu Thr Asp Glu Glu Leu Ala
            100                 105                 110

Asp Trp Lys Arg Arg Pro Glu Ile Ala Cys Ile Gly Gly Pro Pro Asn
            115                 120                 125

Ile Cys Leu Asp Arg Leu Glu Asn Trp Ile Thr Ser Leu Ala Glu Ser
            130                 135                 140

Gln Leu Gln Thr Arg Gln Ile Lys Lys Leu Glu Glu Leu Gln Gln
145                 150                 155                 160

Lys Val Ser Tyr Lys Gly Asp Pro Ile Val Gln His Arg Pro Met Leu
                165                 170                 175

Glu Glu Arg Ile Val Glu Leu Phe Arg Asn Leu Met Lys Ser Ala Phe
            180                 185                 190

Val Val Glu Arg Gln Pro Cys Met Pro Met His Pro Asp Arg Pro Leu
            195                 200                 205

Val Ile Lys Thr Gly
            210
```

```
<210> SEQ ID NO 20
<211> LENGTH: 128
<212> TYPE: PRT
<213> ORGANISM: Mus musculus

<400> SEQUENCE: 20

Val Gln Asp Leu Glu Gln Lys Met Lys Val Val Glu Asn Leu Gln Asp
1               5                   10                  15

Asp Phe Asp Phe Asn Tyr Lys Thr Leu Lys Ser Gln Gly Asp Met Gln
                20                  25                  30

Asp Leu Asn Gly Asn Asn Gln Ser Val Thr Arg Gln Lys Met Gln Gln
            35                  40                  45

Leu Glu Gln Met Leu Thr Ala Leu Asp Gln Met Arg Arg Ser Ile Val
        50                  55                  60

Ser Glu Leu Ala Gly Leu Leu Ser Ala Met Glu Tyr Val Gln Lys Thr
65                  70                  75                  80

Leu Thr Asp Glu Glu Leu Ala Asp Trp Lys Arg Arg Pro Glu Ile Ala
                85                  90                  95

Cys Ile Gly Gly Pro Pro Asn Ile Cys Leu Asp Arg Leu Glu Asn Trp
                100                 105                 110

Ile Thr Ser Leu Ala Glu Ser Gln Leu Gln Thr Arg Gln Gln Ile Lys
                115                 120                 125

<210> SEQ ID NO 21
<211> LENGTH: 95
<212> TYPE: PRT
<213> ORGANISM: Mus musculus

<400> SEQUENCE: 21

Val Gln Asp Leu Glu Gln Lys Met Lys Val Val Glu Asn Leu Gln Asp
1               5                   10                  15

Asp Phe Asp Phe Asn Tyr Lys Thr Leu Lys Ser Gln Gly Asp Met Gln
                20                  25                  30

Asp Leu Asn Gly Asn Asn Gln Ser Val Thr Arg Gln Lys Met Gln Gln
            35                  40                  45

Leu Glu Gln Met Leu Thr Ala Leu Asp Gln Met Arg Arg Ser Ile Val
        50                  55                  60

Ser Glu Leu Ala Gly Leu Leu Ser Ala Met Glu Tyr Val Gln Lys Thr
65                  70                  75                  80

Leu Thr Asp Glu Glu Leu Ala Asp Trp Lys Arg Arg Pro Glu Ile
                85                  90                  95

<210> SEQ ID NO 22
<211> LENGTH: 223
<212> TYPE: PRT
<213> ORGANISM: Mus musculus

<400> SEQUENCE: 22

Val Gln Asp Leu Glu Gln Lys Met Lys Val Val Glu Asn Leu Gln Asp
1               5                   10                  15

Asp Phe Asp Phe Asn Tyr Lys Thr Leu Lys Ser Gln Gly Asp Met Gln
                20                  25                  30

Asp Leu Asn Gly Asn Asn Gln Ser Val Thr Arg Gln Lys Met Gln Gln
            35                  40                  45

Leu Glu Gln Met Leu Thr Ala Leu Asp Gln Met Arg Arg Ser Ile Val
        50                  55                  60

Ser Glu Leu Ala Gly Leu Leu Ser Ala Met Glu Tyr Val Gln Lys Thr
65                  70                  75                  80
```

Leu Thr Asp Glu Glu Leu Ala Asp Trp Lys Arg Arg Pro Glu Ile Ala
              85                  90                  95

Cys Ile Gly Gly Pro Pro Asn Ile Cys Leu Asp Arg Leu Glu Asn Trp
            100                 105                 110

Ile Thr Ser Leu Ala Glu Ser Gln Leu Gln Thr Arg Gln Gln Ile Lys
        115                 120                 125

Lys Leu Glu Glu Leu Gln Gln Lys Val Ser Tyr Lys Gly Asp Pro Ile
    130                 135                 140

Val Gln His Arg Pro Met Leu Glu Glu Arg Ile Val Glu Leu Phe Arg
145                 150                 155                 160

Asn Leu Met Lys Ser Ala Phe Val Val Glu Arg Gln Pro Cys Met Pro
                165                 170                 175

Met His Pro Asp Arg Pro Leu Val Ile Lys Thr Gly Val Gln Phe Thr
            180                 185                 190

Thr Lys Val Arg Leu Leu Val Lys Phe Pro Glu Leu Asn Tyr Gln Leu
        195                 200                 205

Lys Ile Lys Val Cys Ile Asp Lys Asp Ser Gly Asp Val Ala Ala
    210                 215                 220

<210> SEQ ID NO 23
<211> LENGTH: 185
<212> TYPE: PRT
<213> ORGANISM: Mus musculus

<400> SEQUENCE: 23

Gln Ser Val Thr Arg Gln Lys Met Gln Gln Leu Glu Gln Met Leu Thr
  1               5                  10                  15

Ala Leu Asp Gln Met Arg Arg Ser Ile Val Ser Glu Leu Ala Gly Leu
             20                  25                  30

Leu Ser Ala Met Glu Tyr Val Gln Lys Thr Leu Thr Asp Glu Glu Leu
         35                  40                  45

Ala Asp Trp Lys Arg Arg Pro Glu Ile Ala Cys Ile Gly Gly Pro Pro
     50                  55                  60

Asn Ile Cys Leu Asp Arg Leu Glu Asn Trp Ile Thr Ser Leu Ala Glu
 65                  70                  75                  80

Ser Gln Leu Gln Thr Arg Gln Gln Ile Lys Lys Leu Glu Glu Leu Gln
                 85                  90                  95

Gln Lys Val Ser Tyr Lys Gly Asp Pro Ile Val Gln His Arg Pro Met
            100                 105                 110

Leu Glu Glu Arg Ile Val Glu Leu Phe Arg Asn Leu Met Lys Ser Ala
        115                 120                 125

Phe Val Val Glu Arg Gln Pro Cys Met Pro Met His Pro Asp Arg Pro
    130                 135                 140

Leu Val Ile Lys Thr Gly Val Gln Phe Thr Thr Lys Val Arg Leu Leu
145                 150                 155                 160

Val Lys Phe Pro Glu Leu Asn Tyr Gln Leu Lys Ile Lys Val Cys Ile
                165                 170                 175

Asp Lys Asp Ser Gly Asp Val Ala Ala
            180                 185

<210> SEQ ID NO 24
<211> LENGTH: 129
<212> TYPE: PRT
<213> ORGANISM: Mus musculus

<400> SEQUENCE: 24

-continued

Ile Ala Cys Ile Gly Gly Pro Pro Asn Ile Cys Leu Asp Arg Leu Glu
1               5                   10                  15

Asn Trp Ile Thr Ser Leu Ala Glu Ser Gln Leu Gln Thr Arg Gln Gln
            20                  25                  30

Ile Lys Lys Leu Glu Glu Leu Gln Gln Lys Val Ser Tyr Lys Gly Asp
        35                  40                  45

Pro Ile Val Gln His Arg Pro Met Leu Glu Glu Arg Ile Val Glu Leu
    50                  55                  60

Phe Arg Asn Leu Met Lys Ser Ala Phe Val Val Glu Arg Gln Pro Cys
65                  70                  75                  80

Met Pro Met His Pro Asp Arg Pro Leu Val Ile Lys Thr Gly Val Gln
                85                  90                  95

Phe Thr Thr Lys Val Arg Leu Leu Val Lys Phe Pro Glu Leu Asn Tyr
            100                 105                 110

Gln Leu Lys Ile Lys Val Cys Ile Asp Lys Asp Ser Gly Asp Val Ala
            115                 120                 125

Ala

<210> SEQ ID NO 25
<211> LENGTH: 96
<212> TYPE: PRT
<213> ORGANISM: Mus musculus

<400> SEQUENCE: 25

Lys Lys Leu Glu Glu Leu Gln Gln Lys Val Ser Tyr Lys Gly Asp Pro
1               5                   10                  15

Ile Val Gln His Arg Pro Met Leu Glu Glu Arg Ile Val Glu Leu Phe
            20                  25                  30

Arg Asn Leu Met Lys Ser Ala Phe Val Val Glu Arg Gln Pro Cys Met
        35                  40                  45

Pro Met His Pro Asp Arg Pro Leu Val Ile Lys Thr Gly Val Gln Phe
    50                  55                  60

Thr Thr Lys Val Arg Leu Leu Val Lys Phe Pro Glu Leu Asn Tyr Gln
65                  70                  75                  80

Leu Lys Ile Lys Val Cys Ile Asp Lys Asp Ser Gly Asp Val Ala Ala
                85                  90                  95

<210> SEQ ID NO 26
<211> LENGTH: 104
<212> TYPE: PRT
<213> ORGANISM: Rattus sp.

<400> SEQUENCE: 26

Met Thr Ala Lys Met Glu Thr Thr Phe Tyr Asp Asp Ala Leu Asn Ala
1               5                   10                  15

Ser Phe Leu Gln Ser Glu Ser Gly Ala Tyr Gly Ala Tyr Gly Tyr Ser
            20                  25                  30

Asn Pro Lys Ile Leu Lys Gln Ser Met Thr Leu Asn Leu Ala Asp Pro
        35                  40                  45

Val Gly Asn Leu Lys Pro His Leu Arg Ala Lys Asn Ser Asp Leu Leu
    50                  55                  60

Thr Ser Pro Asp Val Gly Leu Leu Lys Leu Ala Ser Pro Glu Leu Glu
65                  70                  75                  80

Arg Leu Ile Ile Gln Ser Ser Asn Gly His Ile Thr Thr Thr Pro Thr
                85                  90                  95

-continued

Pro Thr Gln Phe Leu Cys Pro Lys
            100

<210> SEQ ID NO 27
<211> LENGTH: 230
<212> TYPE: PRT
<213> ORGANISM: Rattus sp.

<400> SEQUENCE: 27

Asn Val Thr Asp Glu Gln Glu Gly Phe Ala Glu Gly Phe Val Arg Gly
 1               5                  10                  15

Leu Ala Glu Leu His Ser Gln Asn Arg Leu Pro Ser Val Thr Ser Ala
            20                  25                  30

Ala Gln Pro Val Ser Gly Ala Gly Met Val Ala Pro Ala Val Ala Ser
        35                  40                  45

Val Ala Gly Ala Gly Gly Gly Tyr Ser Ala Thr Leu Gln Ser Glu
    50                  55                  60

Pro Pro Val Tyr Ala Asn Leu Ser Asn Phe Asn Pro Gly Ala Leu Ser
 65                  70                  75                  80

Thr Gly Gly Gly Ala Pro Ser Tyr Gly Ala Thr Gly Leu Ala Phe Pro
                85                  90                  95

Ser Arg Pro Gln Gln Gln Gln Pro Pro Gln Pro His His Leu
            100                 105                 110

Pro Gln Gln Ile Pro Val Gln His Pro Arg Leu Gln Ala Leu Lys Glu
        115                 120                 125

Glu Pro Gln Thr Val Pro Glu Met Pro Gly Glu Thr Pro Pro Leu Ser
    130                 135                 140

Pro Ile Asp Met Glu Ser Gln Glu Arg Ile Lys Ala Glu Arg Lys Arg
145                 150                 155                 160

Met Arg Asn Arg Ile Ala Ala Ser Lys Cys Arg Lys Arg Lys Leu Glu
                165                 170                 175

Arg Ile Ala Arg Leu Glu Glu Lys Val Lys Thr Phe Lys Ala Gln Asn
            180                 185                 190

Ser Glu Leu Ala Ser Thr Ala Asn Met Leu Arg Glu Gln Val Ala Gln
        195                 200                 205

Leu Lys Gln Lys Val Met Asn His Val Asn Ser Gly Cys Gln Leu Met
    210                 215                 220

Leu Thr Gln Gln Leu Gln
225                 230

<210> SEQ ID NO 28
<211> LENGTH: 229
<212> TYPE: PRT
<213> ORGANISM: Mus musculus

<400> SEQUENCE: 28

Asn His Pro Thr Ala Ala Val Val Thr Glu Lys Gln Gln Met Leu Glu
 1               5                  10                  15

Gln His Leu Gln Asp Val Arg Lys Arg Val Gln Asp Leu Glu Gln Lys
            20                  25                  30

Met Lys Val Val Glu Asn Leu Gln Asp Asp Phe Asp Phe Asn Tyr Lys
        35                  40                  45

Thr Leu Lys Ser Gln Gly Asp Met Gln Asp Leu Asn Gly Asn Asn Gln
    50                  55                  60

Ser Val Thr Arg Gln Lys Met Gln Gln Leu Glu Gln Met Leu Thr Ala
 65                  70                  75                  80

-continued

```
Leu Asp Gln Met Arg Arg Ser Ile Val Ser Glu Leu Ala Gly Leu Leu
                85                  90                  95

Ser Ala Met Glu Tyr Val Gln Lys Thr Leu Thr Asp Glu Glu Leu Ala
            100                 105                 110

Asp Trp Lys Arg Arg Pro Glu Ile Ala Cys Ile Gly Gly Pro Pro Asn
        115                 120                 125

Ile Cys Leu Asp Arg Leu Glu Asn Trp Ile Thr Ser Leu Ala Glu Ser
130                 135                 140

Gln Leu Gln Thr Arg Gln Ile Lys Lys Leu Glu Glu Leu Gln Gln
145                 150                 155                 160

Lys Val Ser Tyr Lys Gly Asp Pro Ile Val Gln His Arg Pro Met Leu
                165                 170                 175

Glu Glu Arg Ile Val Glu Leu Phe Arg Asn Leu Met Lys Ser Ala Phe
            180                 185                 190

Val Val Glu Arg Gln Pro Cys Met Pro Met His Pro Asp Arg Pro Leu
        195                 200                 205

Val Ile Lys Thr Gly Val Gln Phe Thr Thr Lys Val Arg Leu Leu Val
210                 215                 220

Lys Phe Pro Glu Leu
225

<210> SEQ ID NO 29
<211> LENGTH: 229
<212> TYPE: PRT
<213> ORGANISM: Mus musculus

<400> SEQUENCE: 29

Asn His Pro Thr Ala Ala Val Val Thr Glu Lys Gln Gln Met Leu Glu
1               5                   10                  15

Gln His Leu Gln Asp Val Arg Lys Arg Val Gln Asp Leu Glu Gln Lys
            20                  25                  30

Met Lys Val Val Glu Asn Leu Gln Asp Asp Phe Asp Phe Asn Tyr Lys
        35                  40                  45

Thr Leu Lys Ser Gln Gly Asp Met Gln Asp Leu Asn Gly Asn Asn Gln
    50                  55                  60

Ser Val Thr Arg Gln Lys Met Gln Gln Leu Glu Gln Met Leu Thr Ala
65                  70                  75                  80

Leu Asp Gln Met Arg Arg Ser Ile Val Ser Glu Leu Ala Gly Leu Leu
                85                  90                  95

Ser Ala Met Glu Tyr Val Gln Lys Thr Leu Thr Asp Glu Glu Leu Ala
            100                 105                 110

Asp Trp Lys Arg Arg Pro Glu Ile Ala Cys Ile Gly Gly Pro Pro Asn
        115                 120                 125

Ile Cys Leu Asp Arg Leu Glu Asn Trp Ile Thr Ser Leu Ala Glu Ser
130                 135                 140

Gln Leu Gln Thr Arg Gln Ile Lys Lys Leu Glu Glu Leu Gln Gln
145                 150                 155                 160

Lys Val Ser Tyr Lys Gly Asp Pro Ile Val Gln His Arg Pro Met Leu
                165                 170                 175

Glu Glu Arg Ile Val Glu Leu Phe Arg Asn Leu Met Lys Ser Ala Phe
            180                 185                 190

Val Val Glu Arg Gln Pro Cys Met Pro Met His Pro Asp Arg Pro Leu
        195                 200                 205

Val Ile Lys Thr Gly Val Gln Phe Ala Thr Ala Val Ala Leu Leu Val
210                 215                 220
```

```
Lys Phe Pro Glu Leu
225

<210> SEQ ID NO 30
<211> LENGTH: 229
<212> TYPE: PRT
<213> ORGANISM: Mus musculus

<400> SEQUENCE: 30

Asn His Pro Thr Ala Ala Val Val Thr Glu Lys Gln Gln Met Leu Glu
  1               5                  10                  15

Gln His Ala Gln Asp Val Arg Lys Arg Val Gln Asp Leu Glu Gln Lys
             20                  25                  30

Met Lys Val Val Glu Asn Leu Gln Asp Asp Phe Asp Phe Asn Tyr Lys
         35                  40                  45

Thr Leu Lys Ser Gln Gly Asp Met Gln Asp Leu Asn Gly Asn Asn Gln
     50                  55                  60

Ser Val Thr Arg Gln Lys Met Gln Gln Leu Glu Gln Met Leu Thr Ala
 65                  70                  75                  80

Leu Asp Gln Met Arg Arg Ser Ile Val Ser Glu Leu Ala Gly Leu Leu
                 85                  90                  95

Ser Ala Met Glu Tyr Val Gln Lys Thr Leu Thr Asp Glu Glu Leu Ala
            100                 105                 110

Asp Trp Lys Arg Arg Pro Glu Ile Ala Cys Ile Gly Gly Pro Pro Asn
        115                 120                 125

Ile Cys Leu Asp Arg Leu Glu Asn Trp Ile Thr Ser Leu Ala Glu Ser
130                 135                 140

Gln Leu Gln Thr Arg Gln Gln Ile Lys Lys Leu Glu Glu Leu Gln Gln
145                 150                 155                 160

Lys Val Ser Tyr Lys Gly Asp Pro Ile Val Gln His Arg Pro Met Leu
                165                 170                 175

Glu Glu Arg Ile Val Glu Leu Phe Arg Asn Leu Met Lys Ser Ala Phe
            180                 185                 190

Val Val Glu Arg Gln Pro Cys Met Pro Met His Pro Asp Arg Pro Leu
        195                 200                 205

Val Ile Lys Thr Gly Val Gln Phe Thr Thr Lys Val Arg Leu Leu Val
    210                 215                 220

Lys Phe Pro Glu Leu
225

<210> SEQ ID NO 31
<211> LENGTH: 229
<212> TYPE: PRT
<213> ORGANISM: Mus musculus

<400> SEQUENCE: 31

Asn His Pro Thr Ala Ala Val Val Thr Glu Lys Gln Gln Met Leu Glu
  1               5                  10                  15

Gln His Leu Gln Asp Ala Arg Lys Arg Val Gln Asp Leu Glu Gln Lys
             20                  25                  30

Met Lys Val Val Glu Asn Leu Gln Asp Asp Phe Asp Phe Asn Tyr Lys
         35                  40                  45

Thr Leu Lys Ser Gln Gly Asp Met Gln Asp Leu Asn Gly Asn Asn Gln
     50                  55                  60

Ser Val Thr Arg Gln Lys Met Gln Gln Leu Glu Gln Met Leu Thr Ala
 65                  70                  75                  80
```

Leu Asp Gln Met Arg Arg Ser Ile Val Ser Glu Leu Ala Gly Leu Leu
                    85                  90                  95

Ser Ala Met Glu Tyr Val Gln Lys Thr Leu Thr Asp Glu Glu Leu Ala
                100                 105                 110

Asp Trp Lys Arg Arg Pro Glu Ile Ala Cys Ile Gly Pro Pro Asn
                115                 120                 125

Ile Cys Leu Asp Arg Leu Glu Asn Trp Ile Thr Ser Leu Ala Glu Ser
            130                 135                 140

Gln Leu Gln Thr Arg Gln Gln Ile Lys Lys Leu Glu Glu Leu Gln Gln
145                 150                 155                 160

Lys Val Ser Tyr Lys Gly Asp Pro Ile Val Gln His Arg Pro Met Leu
                165                 170                 175

Glu Glu Arg Ile Val Glu Leu Phe Arg Asn Leu Met Lys Ser Ala Phe
                180                 185                 190

Val Val Glu Arg Gln Pro Cys Met Pro Met His Pro Asp Arg Pro Leu
                195                 200                 205

Val Ile Lys Thr Gly Val Gln Phe Thr Thr Lys Val Arg Leu Leu Val
            210                 215                 220

Lys Phe Pro Glu Leu
225

<210> SEQ ID NO 32
<211> LENGTH: 21
<212> TYPE: PRT
<213> ORGANISM: Homo sapien

<400> SEQUENCE: 32

Ala Ala Val Val Thr Glu Lys Gln Gln Met Leu Glu Gln His Leu Gln
1               5                   10                  15

Asp Val Arg Lys Arg
            20

<210> SEQ ID NO 33
<211> LENGTH: 13
<212> TYPE: PRT
<213> ORGANISM: Homo sapien

<400> SEQUENCE: 33

Gly Val Gln Phe Thr Thr Lys Val Arg Leu Leu Val Lys
1               5                   10

<210> SEQ ID NO 34
<211> LENGTH: 21
<212> TYPE: PRT
<213> ORGANISM: Homo sapien

<400> SEQUENCE: 34

Ser Thr Val Met Leu Asp Lys Gln Lys Glu Leu Asp Ser Lys Val Arg
1               5                   10                  15

Asn Val Lys Asp Lys
            20

<210> SEQ ID NO 35
<211> LENGTH: 13
<212> TYPE: PRT
<213> ORGANISM: Homo sapien

<400> SEQUENCE: 35

Gly Val Gln Phe Thr Val Lys Leu Arg Leu Leu Val Lys

-continued

```
          1               5                  10
```

<210> SEQ ID NO 36
<211> LENGTH: 21
<212> TYPE: PRT
<213> ORGANISM: Homo sapien

<400> SEQUENCE: 36

```
Glu Thr Pro Val Glu Ser Gln Gln His Glu Ile Glu Ser Arg Ile Leu
 1               5                  10                  15

Asp Leu Arg Ala Met
            20
```

<210> SEQ ID NO 37
<211> LENGTH: 13
<212> TYPE: PRT
<213> ORGANISM: Homo sapien

<400> SEQUENCE: 37

```
Gly Ser Lys Phe Thr Val Arg Thr Arg Leu Leu Val Arg
 1               5                  10
```

<210> SEQ ID NO 38
<211> LENGTH: 21
<212> TYPE: PRT
<213> ORGANISM: Homo sapien

<400> SEQUENCE: 38

```
Ser Ser Ser Val Ser Glu Arg Gln Arg Asn Val Glu His Lys Val Ala
 1               5                  10                  15

Ala Ile Lys Asn Ser
            20
```

<210> SEQ ID NO 39
<211> LENGTH: 13
<212> TYPE: PRT
<213> ORGANISM: Homo sapien

<400> SEQUENCE: 39

```
Leu Ile Gln Phe Thr Val Lys Leu Arg Leu Leu Ile Lys
 1               5                  10
```

<210> SEQ ID NO 40
<211> LENGTH: 21
<212> TYPE: PRT
<213> ORGANISM: Homo sapien

<400> SEQUENCE: 40

```
His Leu Gln Ile Asn Gln Thr Phe Glu Glu Leu Arg Leu Val Thr Gln
 1               5                  10                  15

Lys Thr Glu Asn Glu
            20
```

<210> SEQ ID NO 41
<211> LENGTH: 13
<212> TYPE: PRT
<213> ORGANISM: Homo sapien

<400> SEQUENCE: 41

```
Gln Thr Lys Phe Ala Ala Thr Val Arg Leu Leu Val Gly
 1               5                  10
```

<210> SEQ ID NO 42

```
<211> LENGTH: 20
<212> TYPE: PRT
<213> ORGANISM: Homo sapien

<400> SEQUENCE: 42

Phe His Asn Lys Gln Glu Glu Leu Lys Phe Lys Thr Gly Leu Arg Arg
  1               5                  10                  15

Leu Gln His Arg
            20

<210> SEQ ID NO 43
<211> LENGTH: 13
<212> TYPE: PRT
<213> ORGANISM: Homo sapien

<400> SEQUENCE: 43

Gln Thr Lys Phe Gln Ala Gly Val Arg Phe Leu Leu Gly
  1               5                  10
```